(12) United States Patent
Spencer et al.

(10) Patent No.: US 10,597,720 B2
(45) Date of Patent: Mar. 24, 2020

(54) APPARATUS, KITS AND METHODS FOR THE PREDICTION OF ONSET OF SEPSIS

(71) Applicant: THE SECRETARY OF STATE FOR DEFENCE, Salisbury, Wiltshire (GB)

(72) Inventors: Phillippa Maria Spencer, Salisbury (GB); Roman Antoni Lukaszewski, Salisbury (GB); Laura Craddock, Salisbury (GB); Helen Eleri Jones, Salisbury (GB)

(73) Assignee: The Secretary of State for Defence, Salisbury, Wiltshire (GB)

( * ) Notice: Subject to any disclaimer, the term of this patent is extended or adjusted under 35 U.S.C. 154(b) by 151 days.

(21) Appl. No.: 15/117,923

(22) PCT Filed: Jan. 9, 2015

(86) PCT No.: PCT/GB2015/000004
§ 371 (c)(1),
(2) Date: Aug. 10, 2016

(87) PCT Pub. No.: WO2015/121605
PCT Pub. Date: Aug. 20, 2015

(65) Prior Publication Data
US 2017/0009297 A1    Jan. 12, 2017

(30) Foreign Application Priority Data
Feb. 11, 2014  (GB) .................................. 1402293.3

(51) Int. Cl.
*C12Q 1/68* (2018.01)
*C12P 19/34* (2006.01)
*C12Q 1/6883* (2018.01)
*G16B 25/00* (2019.01)

(52) U.S. Cl.
CPC ........... *C12Q 1/6883* (2013.01); *G16B 25/00* (2019.02); *C12Q 2600/118* (2013.01); *C12Q 2600/158* (2013.01)

(58) Field of Classification Search
CPC ........ C12Q 2600/158; C12Q 2600/118; G06F 19/20; G06F 19/24; G01N 2800/26
See application file for complete search history.

(56) References Cited

U.S. PATENT DOCUMENTS

| | | | |
|---|---|---|---|
| 2001/0053519 A1* | 12/2001 | Fodor | B01J 19/0046 435/6.11 |
| 2002/0052557 A1 | 5/2002 | Griffin et al. | |
| 2004/0096917 A1 | 5/2004 | Ivey et al. | |
| 2004/0097460 A1 | 5/2004 | Ivey et al. | |
| 2006/0246495 A1 | 11/2006 | Garrett et al. | |
| 2009/0104605 A1 | 4/2009 | Siuzdak et al. | |
| 2009/0186774 A1 | 7/2009 | Turner et al. | |
| 2011/0098195 A1 | 4/2011 | Russwurm | |

FOREIGN PATENT DOCUMENTS

| | | |
|---|---|---|
| EP | 1950310 A1 | 7/2008 |
| GB | 2502759 A | 12/2013 |
| WO | 0052472 A1 | 9/2000 |
| WO | 2006061644 A1 | 6/2006 |
| WO | 2006113529 A1 | 10/2006 |

OTHER PUBLICATIONS

Malone, J.H. et al "Microarrays, deep sequencing and the true measure of the transcriptome" BMC Biology, 9:34 (Year: 2011).*
Talaat A.M. et al. "Genome-directed primers for selective labeling of bacterial transcripts for DNA" Nature Biotechnology, vol. 18, June, p. 679-682. (Year: 2000).*
Vandesompele, J. et al. "Elimination of Primer-Dimer Artifacts and Genomic Coamplification Using a Two-Step SYBR Greenl Real-Time RT-PCR" Analytical Biochemistry 303, 95-98. (Year: 2002).*
Tusher, Virginia Goss, et al., "Significance analysis of microarrays applied to the ionizing radiation response," Proceedings of the National Academy of Sciences of the United States of America (PNAS), Apr. 24, 2001, pp. 5116-5121, vol. 98, No. 9, PNAS, Washington, DC.
Tang, Benjamin M.P., et al: "The Use of Gene-Expression Profiling to Identify Candidate Genes in Human Sepsis," American Journal of Respiratory and Critical Care Medicine, Jun. 15, 2007, pp. 676-684, vol. 176, No. 7, American Thoracic Society, New York, NY.
Illumina: "HumanHT-12 v4 BeadChip Product Information," Jan. 1, 2010, pp. 1-2, XP055178072, Retrieved from the Internet on Mar. 20, 2015, Illumina, San Diego, CA.
Ambion: "Illumina TotalPrep RNA Amplification Kit," Jan. 1, 2011, pp. 1-30, XP055178075, Retrieved from the Internet on Mar. 20, 2015, Life Technologies Corporation (now known as Thermo Fisher Scientific Corporation), Waltham, MA.
United Kingdom Patent Application No. GB1402293.3, Search Report dated Oct. 24, 2014, 4 pages.
International Patent Application No. PCT/GB2015/000004, International Search Report and Written Opinion dated Mar. 27, 2015, 11 pages.
United Kingdom Patent Application No. GB1500306.4, Combined Search and Examination Report dated Oct. 7, 2015, 7 pages.
International Patent Application No. PCT/GB2015/000004, International Preliminary Report on Patentability dated Aug. 25, 2016, 9 pages.
European Patent Application EP 15701566.0, Examination Report dated Jun. 6, 2017, 5 Pages.
Dieffenbach, C. W., et al., "General Concepts for PCR Primer Design," PCR Methods and Applications, 1993, pp. S30-S37, vol. 3, Cold Spring Harbor Laboratory Press.

(Continued)

*Primary Examiner* — Stephen T Kapushoc
(74) *Attorney, Agent, or Firm* — Dean W. Russell; Elena S. Polovnikova; Kilpatrick Townsend & Stockton LLP

(57) ABSTRACT

The present invention provides kits, methods, and apparatus for analysing a biological sample from an animal to predict (pre-symptomatically) and monitor the development of sepsis, utilising biomarker signatures, and especially biomarker signatures capable of providing a mean predictive accuracy of at least 92% to differentiate development of sepsis from non-sepsis.

15 Claims, 4 Drawing Sheets

(56) References Cited

OTHER PUBLICATIONS

De Muro, Marilena Aquino, "Probe Design, Production, and Applications," Medical Biomethods Handbook (Edited by J. M. Walker and R. Rapley), 2005, pp. 13-23, Humana Press, Inc., Totawa, NJ.
United Kingdom Patent Application No. GB 1500306.4, Examination Report dated Apr. 7, 2017, 4 pages.
United Kingdom Patent Application No. GB 1500306.4, Examination Report dated Oct. 25, 2017, 4 pages.
United Kingdom Patent Application No. GB 1807216.5, Combined Search and Examination Report dated May 17, 2018, 8 pages.
European Patent Application No. EP 15701566.0, Office Action dated Jun. 8, 2018, 6 pages.
Japanese Patent Application No. JP 2016-551693, Office Action dated Nov. 27, 2018, 12 pages.
Australian Patent Application No. 2015216742, Examination Report No. 1 dated Jan. 17, 2019.

* cited by examiner

Fig. 4 (Cont.)

| Subset | Abundance threshold | Number of Biomarkers | Median Predictive Accuracy | Subset | Abundance threshold | Number of Biomarkers | Median Predictive Accuracy | Subset | Abundance threshold | Number of Biomarkers | Median Predictive Accuracy | Subset | Abundance threshold | Number of Biomarkers | Median Predictive Accuracy |
|---|---|---|---|---|---|---|---|---|---|---|---|---|---|---|---|
| 1 | 752 | 1 | 65.7 | 21 | 213 | 22 | 91.0 | 41 | 174 | 63 | 95.5 | 61 | 154 | 149 | 94.8 |
| 2 | 343 | 2 | 78.4 | 22 | 210 | 24 | 91.0 | 42 | 173 | 64 | 95.5 | 62 | 153 | 155 | 94.0 |
| 3 | 311 | 3 | 83.6 | 23 | 208 | 25 | 92.5 | 43 | 172 | 66 | 95.5 | 63 | 152 | 162 | 94.0 |
| 4 | 296 | 4 | 83.6 | 24 | 205 | 26 | 93.3 | 44 | 171 | 73 | 94.8 | 64 | 151 | 168 | 94.8 |
| 5 | 270 | 5 | 82.1 | 25 | 203 | 27 | 92.5 | 45 | 170 | 77 | 95.5 | 65 | 150 | 172 | 94.0 |
| 6 | 268 | 6 | 84.3 | 26 | 200 | 28 | 92.5 | 46 | 169 | 79 | 95.5 | 66 | 149 | 176 | 93.3 |
| 7 | 265 | 7 | 84.3 | 27 | 198 | 31 | 95.5 | 47 | 168 | 84 | 95.5 | 67 | 148 | 180 | 93.3 |
| 8 | 258 | 8 | 82.8 | 28 | 197 | 35 | 95.5 | 48 | 167 | 86 | 95.5 | 68 | 147 | 187 | 92.5 |
| 9 | 249 | 9 | 82.8 | 29 | 195 | 37 | 94.0 | 49 | 166 | 93 | 96.3 | 69 | 146 | 191 | 94.0 |
| 10 | 246 | 10 | 86.6 | 30 | 194 | 38 | 95.5 | 50 | 165 | 97 | 97.0 | 70 | 145 | 196 | 92.5 |
| 11 | 245 | 11 | 85.1 | 31 | 189 | 39 | 95.5 | 51 | 164 | 102 | 95.5 | 71 | 144 | 199 | 94.0 |
| 12 | 238 | 13 | 86.6 | 32 | 188 | 40 | 95.5 | 52 | 163 | 109 | 95.5 | 72 | 143 | 203 | 94.0 |
| 13 | 237 | 14 | 91.0 | 33 | 187 | 42 | 95.5 | 53 | 162 | 115 | 95.5 | 73 | 142 | 208 | 92.5 |
| 14 | 234 | 15 | 89.6 | 34 | 184 | 43 | 95.5 | 54 | 161 | 116 | 96.3 | 74 | 141 | 216 | 92.5 |
| 15 | 228 | 16 | 91.0 | 35 | 182 | 49 | 95.5 | 55 | 160 | 121 | 97.0 | 75 | 140 | 221 | 92.5 |
| 16 | 227 | 17 | 91.0 | 36 | 181 | 50 | 95.5 | 56 | 159 | 129 | 95.5 | 76 | 138 | 224 | 92.5 |
| 17 | 224 | 18 | 88.8 | 37 | 180 | 51 | 94.8 | 57 | 158 | 131 | 95.5 | 77 | 137 | 226 | 92.5 |
| 18 | 223 | 19 | 91.0 | 38 | 178 | 54 | 95.5 | 58 | 157 | 133 | 95.5 | 78 | 136 | 229 | 92.5 |
| 19 | 219 | 20 | 91.8 | 39 | 177 | 56 | 94.0 | 59 | 156 | 136 | 97.0 | 79 | 135 | 235 | 92.5 |
| 20 | 216 | 21 | 91.0 | 40 | 175 | 59 | 95.5 | 60 | 155 | 146 | 95.5 | 80 | 134 | 237 | 92.5 |

| Subset | Abundance threshold | Number of Biomarkers | Median Predictive Accuracy |
|---|---|---|---|
| 81 | 133 | 241 | 92.5 |
| 82 | 132 | 244 | 91.0 |
| 83 | 131 | 247 | 91.8 |
| 84 | 130 | 250 | 91.0 |
| 85 | 129 | 251 | 91.0 |
| 86 | 128 | 253 | 91.8 |
| 87 | 127 | 254 | 91.0 |
| 88 | 126 | 256 | 91.0 |
| 89 | 124 | 257 | 92.5 |
| 90 | 123 | 258 | 91.0 |
| 91 | 121 | 259 | 91.0 |
| 92 | 120 | 260 | 91.8 |
| 93 | 110 | 261 | 91.0 |
| 94 | 108 | 262 | 89.6 |
| 95 | 106 | 263 | 89.6 |
| 96 | 101 | 264 | 90.3 |
| 97 | 91 | 265 | 89.6 |
| 98 | 88 | 266 | 89.6 |

APPARATUS, KITS AND METHODS FOR THE PREDICTION OF ONSET OF SEPSIS

CROSS REFERENCE TO RELATED APPLICATION

This application is the U.S. national phase of International Application No. PCT/GB2015/000004 filed on Jan. 9, 2015, and published in English on Aug. 20, 2015 as International Publication No. WO 2015/121605 A1, which application claims priority to Great Britain Patent Application No. 1402293.3 filed on Feb. 11, 2014, the contents of all of which are incorporated herein by reference.

The present invention is concerned with kits, methods and apparatus for analysing a biological sample from an animal to predict and monitor the development of sepsis utilising biomarker, signatures/lists of biomarkers to predict whether an animal is likely to develop the symptoms of sepsis, and especially biomarker signatures capable of providing a mean predictive accuracy of at least 92% to differentiate development of sepsis from non-sepsis, and of at least 95% to differentiate development of sepsis from SIRS.

Following exposure to a biological agent there is often a lag phase before symptoms of sepsis present. After the onset of clinical symptoms, the effectiveness of treatment often decreases as the disease progresses, so the time taken to make any diagnosis is critical. It is likely that a detection or diagnostic assay will be the first confirmed indicator of sepsis. The availability, rapidity and predictive accuracy of such an assay will therefore be crucial in determining the outcome. Any time saved will speed up the implementation of medical countermeasures and will have a significant impact on recovery.

The development of technologies to facilitate rapid detection of biological agent infection is a key concern for all at risk. During the initial stages of infection many biological agents are either absent from, or present at very low concentrations in, typical clinical samples (e.g. blood). It is therefore likely that agent-specific assays would have limited utility in detecting infection before clinical symptoms arise. Previous studies have shown that infection elicits a pattern of immune response involving changes in the expression of a variety of biomarkers that is indicative of the type of agent. Such patterns of biomarker expression have proven to be diagnostic for a variety of infectious agents. It is now possible to distinguish patterns of gene expression in blood leukocytes from symptomatic patients with acute infections caused by four common human pathogens (Influenza A, *Staphylococcus aureus, Streptococcus pneumoniae* and *Escherichia coli*) using whole transcriptome analysis. More recently, researchers have been able to reduce the number of host biomarkers required to make a diagnosis through use of appropriate bioinformatic analysis techniques to select key biomarkers for the diagnosis of infectious disease.

While host biomarker signatures represent an attractive solution for the pre-symptomatic detection of biological agent infection, their discovery relies on the exploitation of laboratory models of infection whose fidelity to the pathogenesis of disease in humans varies. An alternative approach for pre-symptomatic biomarker discovery in humans is to exploit a common sequela of biological agent infection; the life-threatening condition sepsis. Sepsis is traditionally defined as a systemic inflammatory response syndrome (SIRS) in response to infection which, when associated with acute organ dysfunction, may ultimately cause severe life-threatening complications. This broad definition relies on observation of overt symptoms of systemic illness (temperature, blood pressure, heart rate, etc.) as well as the indication of the presence of an infectious organism through microbial culture from clinical samples. It has been described in animal (primarily murine and NHP) models of anthrax (*Bacillus anthracis*), tularemia (*Francisella tularensis*), plague (*Yersinia pestis*), glanders (*Burkholderia mallei*), melioidosis (*B. pseudomallei*), haemorrhagic filovirus and alphavirus infection. More importantly, sepsis is directly caused by the same biological agents in humans.

The incidence of natural biological agent infection is generally extremely low, making prospective studies of the onset of disease in a human population non-viable. However, the development of severe sepsis, associated with organ dysfunction, hypoperfusion or hypotension, is a major cause of morbidity and mortality in intensive care units (ICU). In the UK, severe sepsis is responsible for 27% of all ICU admissions. Across Europe the average incidence of severe sepsis in the ICU is 30%, with a mortality rate of 27%. In the USA, hospital-associated mortality from sepsis ranges between 18 to 30%; an estimated 9.3% of all deaths occurred in patients with sepsis. Clearly there is a very accessible patient population that could be used to study predictive markers for the onset of sepsis.

Despite greatly improved diagnosis, treatment and support, serious infection and sepsis remain significant causes of death and often result in chronic ill-health or disability in those who survive acute episodes. Although sudden, overwhelming infection is comparatively rare amongst otherwise healthy adults, it constitutes an increased risk in immunocompromised individuals, seriously ill patients in intensive care, burns patients and young children. In a proportion of cases, an apparently treatable infection leads to the development of sepsis; a dysregulated, inappropriate response to infection characterised by progressive circulatory collapse leading to renal and respiratory failure, abnormalities in coagulation, profound and unresponsive hypotension and, in about 30% of cases death. The incidence of sepsis in the population of North America is about 0.3% of the population annually (about 750,000 cases) with mortality rising to 40% in the elderly and to 50% in cases of the most severe form, septic shock.

It should be noted that clinical sepsis may also result from infection with some viruses (for example Venezuelan Equine Encephalitis Virus, VEEV) and fungi, and that other mechanisms are likely to be involved in such cases.

The ability to detect potentially serious infections as early as possible and, especially, to predict the onset of sepsis in susceptible individuals is clearly advantageous. A considerable effort has been expended over many years in attempts to establish clear criteria defining clinical entities such as shock, sepsis, septic shock, toxic shock and systemic inflammatory response syndrome (SIRS). Similarly, many attempts have been made to design robust predictive models based on measuring a range of clinical, chemical, biochemical, immunological and cytometric parameters and a number of scoring systems, of varying prognostic success and sophistication, proposed.

According to the 1991 Consensus Conference of the American College of Chest Physicians (ACCP) and Society of Critical Care Medicine (SCCM) "SIRS" is considered to be present when patients have more than one of the following: a body temperature of greater than 38° C. or less than 36° C., a heart rate of greater than 90/min, hyperventilation involving a respiratory rate higher than 20/min or $PaCO_2$ lower than 32 mm Hg, a white blood cell count of greater than 12000 cells/µl or less than 4000 cells/µl.

"Sepsis" has been defined as SIRS caused by infection. It is accepted that SIRS can occur in the absence of infection in, for example, burns, pancreatitis and other disease states. "Infection" was defined as a pathological process caused by invasion of a normally sterile tissue, fluid or body cavity by pathogenic or potentially pathogenic micro-organisms.

"Severe sepsis" is defined as sepsis complicated by organ dysfunction.

"Septic shock" refers (in adults) to sepsis plus a state of acute circulatory failure characterised by a persistent arterial hypotension unexplained by other causes.

The correlation of sepsis and a number of specific serum markers has been extensively studied with a view to developing specific diagnostic and prognostic tests.

However, although many of these markers correlate with sepsis and some give an indication of the seriousness of the condition, no single marker or combination of markers has yet been shown to be a reliable diagnostic test, much less a predictor of the development of sepsis.

Extracting reliable diagnostic patterns and robust prognostic indications from changes over time in complex sets of variables including traditional clinical observations, clinical chemistry, biochemical, immunological and cytometric data requires sophisticated methods of analysis. The use of expert systems and artificial intelligence, including neural networks, for medical diagnostic applications has been being developed for some time.

Neural networks are non-linear functions that are capable of identifying patterns in complex data systems. This is achieved by using a number of mathematical functions that make it possible for the network to identify structure within a noisy data set. This is because data from a system may produce patterns based upon the relationships between the variables within the data. If a neural network sees sufficient examples of such data points during a period known as "training", it is capable of "learning" this structure and then identifying these patterns in future data points or test data. In this way, neural networks are able to predict or classify future examples by modelling the patterns present within the data it has seen. The performance of the network is then assessed by its ability to correctly predict or classify test data, with high accuracy scores, indicating the network has successfully identified true patterns within the data. The parallel processing ability of neural networks is dependent on the architecture of its processing elements, which are arranged to interact according to the model of biological neurones. One or more inputs are regulated by the connection weights to change the stimulation level within the processing element. The output of the processing element is related to its activation level and this output may be non-linear or discontinuous. Training of a neural network therefore comprises an adjustment of interconnected weights depending on the transfer function of the elements, the details of the interconnected structure and the rules of learning that the system follows. Such systems have been applied to a number of clinical situations, including health outcomes models of trauma patients.

US patent application 2002/0052557 describes a method of predicting the onset of a number of catastrophic illnesses based on the variability of the heart-rate of the patient. A neural network is among the possible methods of modelling and analysing the data.

International patent application WO 00/52472 describes a rapid assay method for use in small children based on the serum or neutrophil surface levels of CD11b or 'CD11.b complex' (Mac-1, CR3). The method uses only a single marker, and one which is, arguably, a well-known marker of neutrophil activation in response to inflammation.

The alternative approach to analysing such complex data sets where the data are often qualitative and discrete, rather than quantitative and continuous, is to use sophisticated statistical analysis techniques such as logistic regression. Where logistic regression using qualitative binary dependent variables is insufficiently discriminating in terms of selecting significant variables, multivariate techniques may be used. The outputs from both multiple logistic regression models and neural networks are continuously variable quantities but the likelihoods calculated by neural network models usually fall at one extreme or the other, with few values in the middle range. In a clinical situation this is often helpful and can give clearer decisions.

The ability to detect the earliest signs of infection and/or sepsis has clear benefits in terms of allowing treatment as soon as possible. Indications of the severity of the condition and likely outcome if untreated inform decisions about treatment options. This is relevant both in vulnerable hospital populations, such as those in intensive care, or who are burned or immunocompromised, and in other groups in which there is an increased risk of serious infection and subsequent sepsis. The use or suspected use of biological weapons in both battlefield and civilian settings is an example where a rapid and reliable means of testing for the earliest signs of infection in individuals exposed would be advantageous.

However, until now neither a test nor a list of biomarkers has been identified/produced which can detect or predict sepsis pre-symptomatically with a high predictive accuracy (for example >75%, but preferably >90%).

The present invention thus aims to provide a biomarker signature (list of biomarkers), and methods for classifying biological samples using the biomarker signature, to pre-symptomatically predict/detect the development of sepsis with a high predictive accuracy, and especially a biomarker signature that could differentiate between sepsis and SIRS with an accuracy of at least 95%, and/or differentiate between sepsis and non-sepsis with an accuracy of at least 92%.

With this in mind, the applicants have determined a biomarker signature (list of biomarkers) predictive of the development of sepsis prior to the onset of symptoms (pre-symptomatic) and capable of a mean predictive accuracy of at least 75% to differentiate development of sepsis from non-sepsis, and sepsis from SIRS, wherein the biomarker signature comprises at least 25 genes, or the products expressed by those genes, selected from the list of genes consisting of the 266 genes listed in Table 1. The Applicant has identified through a comprehensive analysis of the host transcriptome, sourced from blood samples from human patients collected prior to the clinical onset of sepsis, a panel of 266 genes (Table 1) highly significant to the onset of symptoms of sepsis. The full panel and subsets thereof were used in a number of statistical models to determine discrimination between sepsis and non-sepsis patients, and between patients with sepsis and SIRS. In order to achieve a mean predictive accuracy of greater than 75%, the Applicant has shown that a signature of at least 25 gene biomarkers can be randomly selected from the 266 genes listed in Table 1.

The Applicant has in particular shown through an analysis of 44,014 combinations/biomarker signatures of 44 biomarkers, randomly selected from the list of 266, that all combinations have a mean predictive accuracy of greater than 75%. These results are illustrated by the 15 specific combinations listed in Table 24, which have the accuracies shown in FIG. 3. Thus in one embodiment the biomarker signature comprises at least 44 genes selected from the list of genes consisting of the 266 genes listed in Table 1.

The Applicant has also identified biomarker signatures, comprising at least 25, at least 44, and comprising all 266 gene biomarkers, which is capable of differentiating development of sepsis from non-sepsis with a mean predictive accuracy of at least 92%, and development of sepsis from SIRS with a mean predictive accuracy of at least 95%.

The Applicant has produced and trained an artificial neural network (ANN) which can provide a predictive accuracy for any selection of biomarkers from the 266 to differentiate between sepsis and non-sepsis and/or sepsis from SIRS predict, and thereby provide a likelihood of whether a patient is to develop sepsis or not through inputting the patient data set into the ANN.

A patient data set, for example that comprising gene expression levels for the 266 biomarkers in a patient blood sample, is inputted into the ANN, having selected a biomarker signature (list of biomarkers), and will thereby output the predictive accuracy of the selected biomarker signature, and also indicate whether the specific patient data set is indicative of the development of sepsis, versus non-sepsis and/or SIRS. The R script for the trained ANN is detailed in Table 2.

The Applicant has shown that a biomarker signature (list of biomarkers) comprising at least 25 genes, but preferably about 44 genes, or the products expressed by those genes, selected from the list of genes consisting of the 266 genes listed in Table 1, as inputted into a mathematical model such as the ANN detailed in Table 2, can be predictive of the development of sepsis prior to the onset of symptoms (pre-symptomatic) and be capable of a mean predictive accuracy of at least 92% to differentiate development of sepsis from non-sepsis.

The Applicant has also shown that a biomarker signature (list of biomarkers) comprising at least 25 genes, but preferably about 44 genes, or the products expressed by those genes, selected from the list of genes consisting of the 266 genes listed in Table 1, as inputted into a mathematical model such as the ANN detailed in Table 2 can be predictive of the development of sepsis prior to the onset of symptoms (pre-symptomatic) and capable of a mean predictive accuracy of at least 95% to differentiate development of sepsis from SIRS. Biomarker signatures providing such high predictive accuracies have not until now been identified, and clearly the use of such signatures could greatly improve the power of kits, apparatuses and methods to be able to identify patients likely to develop sepsis, i.e. presymptomatically, and also to monitor patients with sepsis, and potentially inform patient treatment.

TABLE 1

The 266 gene biomarkers predictive of pre-symptomatic development of sepsis, as down-selected from the whole transcriptome using a multitude of mathematical methods.

| | | | | | | |
|---|---|---|---|---|---|---|
| ACTR6 | EBI2 | CXORF42 | SORBS3 | RPL11 | SLC26A8 | ATP2A2 |
| BIN1 | GAS7 | CLASP1 | TIMM9 | PPP2R2B | WDR37 | ZNF608 |
| C16ORF7 | HIST2H4B | CD2 | TST | NOL11 | ZNF17 | TBC1D8 |
| CD247 | IL1R1 | C14ORF112 | CCDC65 | GZMK | ANKS1A | RRBP1 |
| CLNS1A | LGALS2 | BCL6 | NCOA3 | ZNF32 | CD59 | RPL26 |
| CYB561 | LTA | MRPL24 | PDCD4 | TMEM42 | EIF3D | PHCA |
| FCER1A | EEF1B2 | LOC646483 | RASGRP1 | TCEA3 | GYG1 | NSUN7 |
| GRB10 | CTSS | KLRG1 | RPL18A | SLC2A11 | KIF1B | LETMD1 |
| HS.445036 | CD7 | HLA-DRA | RPS14 | SERTAD2 | MMP9 | IRAK3 |
| LARP5 | CACNA1E | GRAMD4 | RPS6 | RPS20 | PAG1 | FAM160A2 |
| LOC646766 | C12ORF57 | MRPS6 | SIVA | RPL38 | RPL19 | CTDP1 |
| MRPL50 | AOC2 | OLFML2B | SS18L2 | RPL12 | RPS15 | ATP8B4 |
| ADRB2 | LY6E | PTPRCAP | TMC6 | PRKCQ | SLC36A1 | RPS3A |
| BOAT | LOC285176 | RPL13 | TTLL3 | OLFM1 | WWP1 | TDRD9 |
| C21ORF7 | IL1R2 | RPL7A | CDO1 | HLA-DRB3 | ARG1 | RUNX1 |
| CD3D | HLA-DMA | RPS27 | RPSA | ZNF430 | CKAP4 | RPL27A |
| CPA3 | GBP1 | SH2D1A | RPS15A | TOMM7 | EMILIN2 | PHTF1 |
| DHRS3 | EOMES | SMAD2 | RPL30 | TCTN1 | HIBADH | NT5DC2 |
| FLT3LG | CUTL1 | THBS3 | RCN2 | SLC38A10 | MUC1 | LOC153561 |
| GTPBP8 | CD96 | TP53BP2 | PECI | ACVR1B | PFKFB2 | ITGAM |
| ICAM2 | CCL5 | ZNHIT3 | NDST2 | C13ORF23 | RPL22 | FBXO34 |
| LDHA | C12ORF62 | LEPROTL1 | EFCBP1 | DACH1 | RPS25 | CYP1B1 |
| LOC652071 | ASNSD1 | MS4A4A | ZFAND1 | FBXW2 | SLC41A3 | ATXN7L3 |
| MRPS27 | MAFG | P117 | TMEM150 | ITGAX | ZC3H3 | TRPM2 |
| AKR1B1 | LOC644096 | PYHIN1 | SSBP2 | LOC647099 | NAPB | RPL4 |
| BTBD11 | IL32 | RPL13A | SLBP | OPLAH | LARP4B | PLAC8 |
| C5ORF39 | HLA-DMB | RPL9 | RTP4 | PTPN1 | HIPK2 | |
| CD3E | GBP4 | RPS29 | RPS17 | RPL5 | EXOC7 | |
| CR1 | EXOSC5 | SIGIRR | RPL32 | SIL1 | CMTM4 | |
| DIP2A | CXORF20 | SMPDL3A | RPL10A | UPP1 | ARID5B | |
| GALM | CDKN2AIP | THNSL1 | POP5 | TFB1M | ZDHHC19 | |
| HDC | CD177 | TRAT1 | NMT2 | AMD1 | SORT1 | |
| ICOS | C12ORF65 | OSTALPHA | FAM26F | C22ORF9 | RPS8 | |
| LDOC1 | ATP9A | MYBPC3 | ZNF195 | DNAJC5 | RPL24 | |
| LSG1 | METTL7B | P2RY5 | TMEM204 | GOLGA1 | PGD | |
| AMPH | LOC646200 | RARRES3 | TBCC | KIAA1881 | NLRC4 | |
| C11ORF1 | ITM2A | RPL18 | SLC26A6 | MACF1 | LDLR | |
| C9ORF103 | HLA-DPA1 | RPS10 | SELM | P4HB | HK3 | |
| CD6 | GPR107 | RPS5 | RPS18 | RPL15 | EXT1 | |
| CRIP2 | FAM69A | SIRPG | RPL36 | RPS13 | CSGALNACT2 | |

TABLE 2

The R script for a trained artificial neural network (ANN) for calculating the predictive accuracy for a biomarker signature selected from the 266 biomarkers to differentiate development of sepsis versus non-sepsis and/or SIRS, and thereby indicate the likelihood that a patient data set inputted into the ANN is indicative of the development of sepsis or not.

```
# DATA PROCESSING:
            rawdata <- read.csv("Data/44 top performing genes.csv")
            transposed <- data.frame(t(rawdata[,-1 ]))
            names(transposed) <- c("Diagnosis", "Day",
as.character(rawdata$SAMPLE_ID[3:nrow(rawdata)]))
            transposed$Diagnosis <- factor(transposed$Diagnosis, levels=c(0,1), labels=c("No
Sepsis", "Sepsis"))
            for.normalising <- transposed[ ,3:ncol(transposed)]
            not.for.normalising <- transposed[ ,1:2]
            medians <- apply(for.normalising, 2, median)
            normalised.genes <- sweep(data.matrix(for.normalising), 2, medians)
            normalised.data <- data.frame(not.for.normalising, normalised.genes)
            input <- normalised.data[ ,-2]
# TRAINING/TEST SPLIT:
            cases <- nrow(input)
            cases.train <- sample(1:cases, round((0.7*cases), digits =0))
            training <- input[cases.train, ]
            test <- input[-cases.train, ]
# NEURAL NETWORK:
            library(nnet)
            nntraining <- nnet(Diagnosis ~ ., data = training, size = 1, rang = 1,
                        decay = 0.01, maxit = 1000, Hess = FALSE, MaxNWts = 1000,
                        abstol = 1.0e-4, reltol = 1.0e-8, trace = TRUE,
                        skip = FALSE, lineout = FALSE, softmax = FALSE, censored =
FALSE,
                        entropy = TRUE)
                        #Unused nnet arguments: weights = 1, Wts = 1, mask = all,
entropy = FALSE
            Outcome <- test$Diagnosis
            nn_Prediction <- predict(nntraining, test, type = "class")
            dfAll <- data.frame(Outcome, nn_Prediction)
            prediction.table <- xtabs(~Outcome+nn_Prediction, data=dfAll)
            c(prediction.table[1,1] + prediction.table[2,2] , prediction.table[1,2],
prediction.table[2,1])/nrow(test)
```

Preferred biomarker signatures for use in the present invention are those that result in a mean predictive accuracy of at least 92% to differentiate development of sepsis from non-sepsis, or a mean predictive accuracy of at least 95% to differentiate development of sepsis from SIRS which can be identified by a simple iterative approach, inputting biomarker signatures into a mathematical model, such as the trained ANN detailed in table 2. The Applicant has in particular used this approach to identify a key biomarker signature of 44 biomarkers which can differentiate sepsis from SIRS with 100% predictive accuracy, and sepsis from SIRS with 97% predictive accuracy Accordingly, in a first aspect, the present invention provides a diagnostic kit for predicting the development of sepsis prior to the onset of symptoms (pre-symptomatic), said kit comprising means for detecting levels of a gene or gene product of each member of a biomarker signature in a sample, wherein the biomarker signature comprises at least 25 genes, or the products expressed by those genes, selected from the list of genes consisting of the 266 genes listed in Table 1.

The biomarker signature may be capable of a mean predictive accuracy of at least 75% to differentiate development of sepsis from non-sepsis, and sepsis from SIRS, though particularly advantageously the biomarker signature is capable of a mean predictive accuracy of at least 92% to differentiate development of sepsis from non-sepsis, and/or a mean predictive accuracy of at least 95% to differentiate development of sepsis from non-sepsis.

Microarray technology was used to obtain gene expression data of samples derived from pre-symptomatic sepsis patients and control non-sepsis patient samples. An unsupervised bioinformatic approach was used to identify prognostic transcriptomic expression patterns that characterize sepsis before the onset of clinical symptoms. These characteristic biomarker patterns were further analysed and validated using quantitative RT-PCR.

The Applicant has shown that use of all 266 biomarkers provides a predictive accuracy of more than 95% to differentiate both the development of sepsis from non-sepsis and sepsis from SIRS. A selection of 44 biomarkers from the 266 can potentially provide a predictive accuracy up to 100% to differentiate the development of sepsis from SIRS, and a predictive accuracy of at least 97% to differentiate the development of sepsis from non-sepsis.

The Applicant has in particular identified a biomarker signature containing 44 biomarkers, the list consisting of those biomarkers in Table 3, which when all 44 biomarkers are used for the prediction is capable of up to 100% predictivity of sepsis versus SIRS. Use of a specific list of 25 biomarkers down-selected from these 45, as listed in Table 3, is capable of a predictive accuracy of at least 92% to differentiate development of sepsis from non-sepsis, and at least 95% to differentiate development of sepsis from SIRS. These predictive accuracies are in particular obtainable using the artificial neural network detailed in Table 2, though such accuracies may be obtained using other mathematical models, and other artificial neural networks.

TABLE 3

Specific (first) biomarker signature consisting of 44 biomarkers selected from the 266 gene biomarkers, and a further down-selected list of 25 biomarkers.

| 44 Gene Biomarker Signature | Down-selected 25 Gene Biomarker Signature |
|---|---|
| ACTR6, BIN1, C16ORF7, CD247, CLNS1A, CYB561, FCER1A, GRB10, HS.445036, LARP5, LOC646766, MRPL50, ADRB2, BOAT, C21ORF7 CD3D, CPA3, DHRS3, FLT3LG, GTPBP8, ICAM2, LDHA, LOC652071, MRPS27, AKR1B1, BTBD11, C5ORF39, CD3E, CR1, DIP2A, GALM, HDC, ICOS, LDOC1, LSG1, AMPH, C11ORF1, C9ORF103, CD6, CRIP2, EBI2, GAS7, HIST2H4B, IL1R1 | ACTR6, BIN1, C16ORF7, CD247, CLNS1A, CYB561, FCER1A, GRB10, HS.445036, LARP5, LOC646766, MRPL50, ADRB2, BOAT, C21ORF7 CD3D, CPA3, DHRS3, FLT3LG, GTPBP8, ICAM2, LDHA, LOC652071, MRPS27, AKR1B1 |

A further list of 45 gene biomarkers selected from the list of 266 as detailed in Table 4, was also shown to have a predictivity of higher than 92% to differentiate sepsis from non-sepsis, especially with a specific down-selected list of 25 biomarkers.

TABLE 4

Further (second) specific biomarker signature consisting of 45 biomarkers selected from the 266 gene biomarkers, and a further down-selected list of 25 biomarkers.

| 45 Gene Biomarker Signature | Down-selected 25 Gene Biomarker Signature |
|---|---|
| ATP9A, C16ORF7, C5ORF39, C9ORF103, CACNA1E, CD177, DHRS3, EEF1B2, FCER1A, FLT3LG, GAS7, GRB10, HLA.DMA, HS.445036, IL1R1, IL1R2, LOC285176, MYBPC3, NCOA3, NDST2, RPL10A, EBI2, LOC646483, RPL13A, RPL18, RPL18A, RPL32, RPL36, RPL9, RPS20, RPS29, RPS6, SIGIRR, SLBP, SLC26A6, SMPDL3A, SORBS3, TCEA3, TCTN1, THBS3, THNSL1, TIMM9, TOMM7, ZFAND1, ZNHIT3 | C16ORF7, C5ORF39, C9ORF103, CD177, FCER1A, GAS7, LOC285176, MYBPC3, NDST2, EBI2, RPL13A, RPL18A, RPL32, RPL36, RPL9, RPS20, RPS29, RPS6, SIGIRR, TCEA3, TCTN1, TIMM9, TOMM7, ZFAND1, ZNHIT3 |

These further (second) two biomarker signatures of 45 and 25 have 11 and 6 biomarkers, respectively, in common with the first 44 gene biomarker signature. The Applicant has also evaluated 14 further combinations of 44 biomarkers in detail, of which all combinations have a mean predictive accuracy of at least 75%, but of which 6 combinations have a mean predictive accuracy of at least 92%. These signatures are listed in Table 5. These six signatures have at least 5 genes in common with the first 44 gene biomarker signature in Table 3, and thus in one embodiment any combination of 44 biomarkers or 25 biomarkers selected from the 266 may comprise at least 5 biomarkers from the first 44 in order to provide a mean predictive accuracy of at least 92%.

In another embodiment, the at least 25 genes comprises at least 11 genes selected from the first 44 gene biomarker signature. In a third embodiment the at least 25 genes comprises at least the complete first 25 gene biomarker signature (listed in Table 3). In a fourth embodiment, the biomarker signature of the present invention comprises the complete first 44 gene biomarker signature (listed in Table 3).

TABLE 5

Six combinations of 44 biomarkers selected from the list of 266 biomarkers which have a mean predictive accuracy of sepsis vs non-sepsis of at least 92% by using the artificial neural network detailed in Table 2

| 1 | 2 | 3 | 4 | 5 | 6 |
|---|---|---|---|---|---|
| CYB561 | ACTR6 | C16ORF7 | CD6 | BCL6 | EBI2 |
| GRB10 | BIN1 | LARP5 | CD247 | CLNS1A | CD247 |
| BTBD11 | LOC646766 | C21ORF7 | CLNS1A | CYB561 | FCER1A |
| CD3E | ICAM2 | GTPBP8 | C5ORF39 | FCER1A | ICAM2 |
| EBI2 | LOC652071 | LDHA | GALM | C21ORF7 | C5ORF39 |
| CD7 | ICOS | MRPS27 | ICOS | FLT3LG | EEF1B2 |
| LOC285176 | CD7 | BTBD11 | AOC2 | CTSS | C12ORF57 |
| HLA-DMA | IL1R2 | HDC | IL1R2 | CD96 | AOC2 |
| C12ORF62 | ASNSD1 | CRIP2 | CUTL1 | CCL5 | EOMES |
| ASNSD1 | MAFG | IL1R1 | CDKN2AIP | HLA-DMB | IL32 |
| GPR107 | GBP4 | CACNA1E | ITM2A | CDKN2AIP | GBP4 |
| BCL6 | CXORF20 | LOC285176 | CLASP1 | GPR107 | CD177 |
| MRPL24 | HLA-DPA1 | HLA-DMA | C14ORF112 | CXORF42 | HLA-DPA1 |
| RPL7A | CXORF42 | ASNSD1 | BCL6 | CLASP1 | C14ORF112 |
| RPL13A | MRPL24 | LOC644096 | LOC646483 | RPS27 | BCL6 |
| RPS5 | PTPRCAP | IL32 | RPS27 | SMAD2 | MRPL24 |
| CCDC65 | RPL7A | FAM69A | P117 | ZNHIT3 | RPS27 |
| NCOA3 | PYHIN1 | MRPL24 | RPL9 | RPL13A | P117 |
| RASGRP1 | RASGRP1 | HLA-DRA | RPS10 | SMPDL3A | NCOA3 |
| RPS6 | RPL30 | MRPS6 | SORBS3 | TMEM150 | RASGRP1 |
| NMT2 | EFCBP1 | RPS27 | TST | FAM26F | RPS6 |
| ZNF32 | TMEM150 | PYHIN1 | RPL18A | TBCC | PECI |
| SERTAD2 | RPL32 | SIGIRR | SS18L2 | TCEA3 | EFCBP1 |
| RPL38 | ZNF195 | SMPDL3A | CDO1 | ITGAX | TMEM150 |
| SLC38A10 | TMEM204 | P2RY5 | RPS15A | PTPN1 | NMT2 |

TABLE 5-continued

Six combinations of 44 biomarkers selected from the list of 266 biomarkers which have a mean predictive accuracy of sepsis vs non-sepsis of at least 92% by using the artificial neural network detailed in Table 2

| 1 | 2 | 3 | 4 | 5 | 6 |
|---|---|---|---|---|---|
| ACVR1B | SELM | RARRES3 | TMEM150 | TFB1M | SLC26A6 |
| P4HB | RPS18 | TTLL3 | RPL32 | AMD1 | RPL11 |
| SLC26A8 | PPP2R2B | RPS15A | SLC26A6 | KIAA1881 | PPP2R2B |
| WDR37 | OLFM1 | RPL36 | RPS20 | CD59 | ZNF32 |
| PAG1 | TCTN1 | TMEM42 | HLA-DRB3 | KIF1B | ACVR1B |
| RPL19 | DACH1 | HLA-DRB3 | TCTN1 | RPL19 | TFB1M |
| SLC41A3 | ITGAX | FBXW2 | P4HB | NAPB | P4HB |
| LARP4B | TFB1M | LOC647099 | RPL15 | ZDHHC19 | RPL15 |
| ZDHHC19 | GYG1 | ZNF17 | RPS13 | EXT1 | ZNF17 |
| SORT1 | MMP9 | CD59 | WDR37 | ZNF608 | EIF3D |
| NLRC4 | PAG1 | KIF1B | ANKS1A | TBC1D8 | MMP9 |
| EXT1 | RPS15 | SLC36A1 | KIF1B | RRBP1 | SLC36A1 |
| ATP2A2 | CKAP4 | PFKFB2 | MMP9 | ATP8B4 | NAPB |
| ZNF608 | RPL22 | SLC41A3 | EXOC7 | RPS3A | ARID5B |
| RRBP1 | ZDHHC19 | EXOC7 | CMTM4 | RPL27A | HK3 |
| TDRD9 | SORT1 | HK3 | RPL24 | PHTF1 | CSGALNACT2 |
| RUNX1 | NLRC4 | ATP2A2 | CSGALNACT2 | FBXO34 | FAM160A2 |
| LOC153561 | CSGALNACT2 | LETMD1 | ATP2A2 | CYP1B1 | RPS3A |
| ITGAM | RRBP1 | ITGAM | FAM160A2 | RPL4 | RPL27A |

In a second aspect, the present invention provides a method for analysis of a biological sample from an animal to predict and monitor the development of sepsis, especially prior to onset of symptoms, comprising monitoring, measuring and/or detecting the expression of all biomarkers in the selected biomarker signature (list of biomarkers), and evaluating/assessing data produced from the monitoring, measuring and/or detecting to predict and monitor the development of sepsis.

The method is preferably capable of differentiating sepsis from non-sepsis, with high levels of accuracy, such as >75%, but preferably >90% accuracy, or as high as >92%, and also potentially sepsis from SIRS with the same predictivities.

The animal may be a human, and the biological sample is most likely a blood or serum sample.

The diagnostic kit of the invention provides the means for detecting levels of a gene or gene product of the genes comprising the biomarker signatures described above. Although gene expression may be determined by detecting the presence of gene products including proteins and peptides, such processes may be complex. In a particular embodiment, the means comprises means for detecting a nucleic acid and in particular DNA, or a gene product which is RNA such as mRNA.

The monitoring, measuring or detecting may use any suitable technique, including use of recognition elements, or microarray based methods. Thus in a particular embodiment, the kit of the invention comprises microarray on which are immobilised probes suitable for binding to RNA expressed by each gene of the biomarker signature.

In an alternative embodiment, the kit comprises at least some of the reagents suitable for carrying out amplification of genes or regions thereof, of the biomarker signature.

In one embodiment the monitoring, measuring or detecting the expression of biomarkers uses real-time (RT) polymerase chain reaction (PCR). In such cases, the means may comprise primers for amplification of said genes or regions thereof. The kits may further comprise labels in particular fluorescent labels and/or oligonucleotide probes to allow the PCR to be monitored in real-time using any of the known assays, such as TaqMan, LUX, etc. The kits may also contain reagents such as buffers, enzymes, salts such as MgCl etc. required for carrying out a nucleic acid amplification reaction.

The method of the second aspect is advantageously computer-implemented to handle the complexity in monitoring and analysis of the numerous biomarkers, and their respective relationships to each other. Such a computer implemented invention could enable a yes/no answer as to whether sepsis is likely to develop, or at least provide an indication of how likely the development of sepsis is.

The method preferably uses mathematical modelling tools and/or algorithms to monitor and assess expression of the biomarkers both qualitatively and quantitatively. The tools could in particular include support vector machine (SVM) algorithms, decision trees, random forests, artificial neural networks, quadratic discriminant analysis, and Bayes classifiers. In a preferred embodiment the data from monitoring all biomarkers in the biomarker signature is assessed by means of an artificial neural network, for example the trained artificial neural network detailed in Table 2.

In one embodiment of the second aspect the method is a computer-implemented method wherein the monitoring, measuring and/or detecting comprises producing quantitative, and optionally qualitative, data for all biomarkers, inputting said data into an analytical process on the computer, using at least one mathematical method, that compares the data with reference data, and producing an output from the analytical process which provides a prediction for the likelihood of developing sepsis, or enables monitoring of the sepsis condition. The reference data may include data from healthy subjects, subjects diagnosed with sepsis, and subjects with SIRS, but no infection.

The output from the analytical process may enable the time to onset of symptoms to be predicted, such as 1, 2, or 3 days prior to onset of symptoms, and consequently may be particularly valuable and useful to a medical practitioner in suggesting a course of treatment, especially when the choice of course of treatment is dependent on the progression of the disease. The method may also enable monitoring of the success of any treatment, assessing whether the likelihood of onset of symptoms decreases over the course of treatment.

In a third aspect, the present invention provides an apparatus for analysis of a biological sample from an animal to predict and monitor the development of sepsis comprising means for monitoring, measuring or detecting the expression of all biomarkers in the biomarker signature as described above, such as RT-PCR using reagents specific to the biomarkers in the biomarker signature, and means for analysis of data produced from the means for monitoring, measuring or detecting, such as a computer comprising an appropriate mathematical model to analyses the data, such as an artificial neural network, and means for providing an output from the analysis which output provides a prediction of the likelihood of an animal having sepsis, or an output to enable monitoring of sepsis, which output could also be provided by an appropriately programmed computer.

The present invention will now be described with reference to the following non-limiting examples and drawings.

Figure 1:
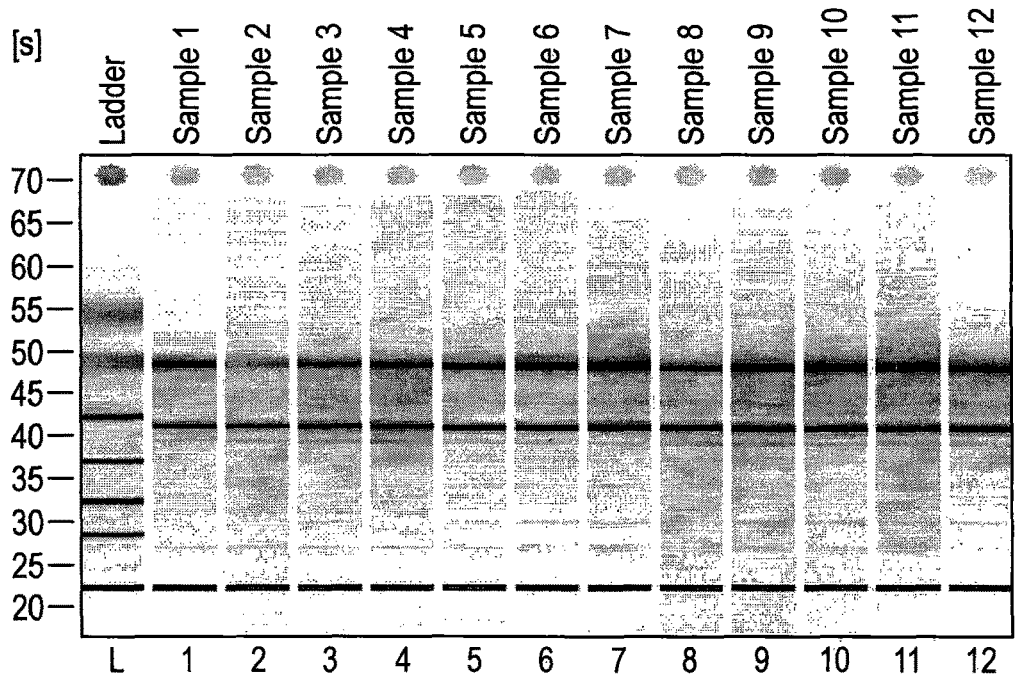
FIG. 1 is a display of Bioanalyzer results for a randomised selection of RNA sample preparations.

EXAMPLE—DEVELOPMENT OF A PREDICTIVE PANEL OF PRE-SYMPTOMATIC BIOMARKERS FOR SEPSIS

The aim of this program of work was to develop a predictive panel of pre-symptomatic biomarkers for sepsis, through comprehensive analysis of the host transcriptome, sourced from blood samples from human patients collected prior to the clinical onset of sepsis, and to develop biomarker signatures that may indicate whether and when clinical symptoms will arise following infection. In so doing it would yield a suitably powered bioinformatic model for differentiating sepsis patients from control patients based on transcriptomic biomarker signatures. In turn, this will assist in the development of RT-PCR methods for sepsis prediction, where this capability should provide timely diagnosis and treatment of infection when medical countermeasures are most effective.

We used microarray technology to obtain gene expression data of samples derived from pre-symptomatic sepsis patients and control non-sepsis patient samples. An unsupervised bioinformatic approach was used to identify prognostic transcriptomic expression patterns that characterize sepsis before the onset of clinical symptoms. These characteristic biomarker patterns were further analysed and validated using quantitative RT-PCR on the Fluidigm BioMark™ real-time PCR array platform.

Through significance testing a final panel of 266 biomarkers was derived. The full panel and subsets of this was then used in a number of statistical models to determine discrimination between sepsis and non-sepsis patients. The artificial neural network gave the highest predictive accuracy, with 44 biomarkers being the optimal subset.

Technical Summary

Acquisition and Storage of Patient Samples—

Patients were admitted to the study if they gave informed consent, were between 18 and 80 years of age and undergoing a procedure that, in the clinician's opinion, had a risk of causing infection and ultimately sepsis. Typically these were abdominal and thoracic surgeries. However, other surgical procedures were permitted and included, with one extensive maxillofacial procedure resulting in sepsis in one case. Patients were excluded if they were either pregnant, infected with a known pathogen (HIV, Hepatitis A, B or C), immunosuppressed or withdrew consent to take part in the study at any time during their stay. All patients received the normal standard of care once enrolled.

Blood samples were collected according to a protocol. Briefly, two 4 ml aliquots of patient blood were collected into sterile EDTA vacutainers and then immediately transferred into RNAse-free vials containing 10.5 ml of RNA/Ater® (a RNA stabilization media) (Life Technologies, USA). These were then stored at −20° C. and eventually transported on dry ice. In addition 4 ml of patient blood was collected into a serum separation tube, spun, separated and stored at −20 C. Blood collection occurred once between 1 and 7 days before surgery and then once daily on each day post-surgery. Post-operative blood collection was stopped after the patient was discharged from hospital, or after 7 days post-surgery, or once sepsis had been confirmed by the clinician. Additional patient information (e.g. daily patient metrics, type of surgery and microbiology results) was captured using a bespoke database provided by ItemTracker, UK.

We recruited 2273 elective surgery patients into the study with 1842 patient time courses in storage; 72 of these patients went on to develop sepsis. The incidence of sepsis in our patient cohort is therefore 3.91%. Over 600 of the remaining patients met the criteria set for SIRS (2 out of the following four symptoms: increased/decreased temperature; increased heart rate; increased ventilation rate, increased/decreased white blood cell count). However, many of these "SIRS" patients had very transient changes in symptomology. We suspect that the 438 patients, as identified by the clinical staff at the centres, are more reflective of the number of patients with prolonged SIRS.

This patient recruitment was sufficient to satisfy the requirement for 30 sepsis patient time courses (plus matched non-sepsis patient controls) to be used for biomarker discovery during 2011 as well as a further 40 sepsis patients time courses (plus matched non-sepsis patient controls) for the validation of biomarkers during 2012.

An initial batch of 61 SIRS patient blood samples was analysed. Of these samples, 2 were identified as having microbial DNA present in the blood (one patient had *E. coli* and the other had *S. aureus*). These patients were re-classified as belonging to the patient cohort that goes on to develop sepsis. The remaining 59 patients had undetectable levels of microbial DNA present in their blood. This indicated that these patients truly belonged to the SIRS patient group. The biomarker signatures from both groups of patients were then used in a biomarker discovery analysis that provided a biomarker signature for the pre-symptomatic diagnosis of sepsis in elective surgery patients. A second batch of 190 patient samples containing samples from patients who developed either SIRS or sepsis, as well as samples from patients who did not develop any post-surgical symptoms (post-operative controls) were again sent for analysis using the Sepsitest. All post-operative control patient samples were confirmed as negative by the Sepsitest. Additionally all the patient samples isolated from sepsis patients with blood borne infections were also identified correctly. All of the SIRS patients were confirmed as not septic.

RNA Extraction from Stabilization Media—

The RNA from all patient samples selected for further microarray and Fluidigm array analysis was extracted using the RiboPure™-Blood kit (Life Technologies, USA), followed by treatment with TURBO DNA-Free™ (Life Technologies, USA). In order to give confidence in the quality of sample preparation the quality of all RNA products were assessed on the Agilent 2100 BioAnalyser (Agilent USA) using the Agilent BioAnalyser RNA 6000 Nano kit (Agilent USA). Having regard to FIG. 1 a qualitative indication of the 100s of RNA samples using 12 randomly selected samples is shown using the Agilent 2100 BioAnalyser (Agilent USA). The double banding in each lane indicates good quality RNA with little degradation. Further quantitative measures of the quality and quantity of RNA preparation, like the RNA integrity number (RIN), and concentration of RNA in each preparation indicated that RNA isolation protocols were fit for purpose (Table 6).

TABLE 6

Quantification and integrity of typical RNA samples. Results

| Patient sample | RIN Result | Concentration (µg/ml) | Total concentration | Did the sample pass QC (RIN >7.0/RNA >2.0)? |
|---|---|---|---|---|
| 1 | 8.0 | 49 | 4.41 | Yes |
| 2 | 7.0 | 23 | 2.07 | Yes |
| 3 | 7.0 | 36 | 3.24 | Yes |
| 4 | 7.5 | 34 | 3.06 | Yes |
| 5 | 8.5 | 28 | 2.52 | Yes |
| 6 | 8.9 | 30 | 2.70 | Yes |
| 7 | 8.4 | 50 | 4.50 | Yes |
| 8 | 7.3 | 30 | 2.70 | Yes |
| 9 | 7.3 | 45 | 4.05 | Yes |
| 10 | 7.9 | 48 | 4.32 | Yes |
| 11 | 7.5 | 38 | 3.42 | Yes |
| 12 | 7.8 | 47 | 4.23 | Yes |

Over 99% of RNA samples achieved a RIN of 7 or above with a yield of 2 µg or above. This was sufficient quality and quantity to undertake microarray and quantitative RT-PCR analyses on these samples. On the rare occasions when the sample preparations gave an unsatisfactory yield, the process was repeated four times and the product sent for quantitative RT-PCR only (i.e. there was sufficient RNA to produce cDNA and subsequently undertake PCR).

The selection of those patients who went on to develop sepsis and those that did not was the responsibility of the Principal Investigators (PIs) at each centre. They were all consultant intensive care clinicians with many years' experience in the clinic with over 265 peer review publications between them. Two of the four PIs from the four centres hold prominent advisory roles to journals and funding bodies across Europe and the USA. Selections by the clinicians were double-checked by the project team to ensure that all patients met the previously agreed criteria for the definition of sepsis. Peri-operative antibiotic use was minimal, with only one dose of a broad-spectrum antibiotic given in 85.7% of sepsis patient cases, prior to sepsis diagnosis. The remaining patients received daily doses of antibiotic but still developed clinical evidence of sepsis. Under clinical guidance we have included these patients in the study as they developed sepsis in spite of treatment, although it is possible that such treatment may have influenced microbial culture results. The range of infectious agents that resulted in sepsis in the study was quite broad and is listed in Table 7.

TABLE 7

Infectious agents isolated from sepsis patients in phase I and II of the study.

| Phase 1 - Discovery | | Phase II - Validation | |
|---|---|---|---|
| Escherichia coli | Blood Serratia | Haemophilus influenzae | Enterobacter species |
| Pseudomonas aeruginosa | Candida species | Escherichia coli | Stenotrophomonas maltophilia |
| Klebsiella species | Proteus species | Klebsiella species | Gram negative bacilli |
| coliforms | Clostridium difficile | Pseudomonas aeruginosa | Candida species |
| Streptococcus pneumoniae | | Streptococcus pneumoniae | coliforms |
| Staphylococcus aureus | | Staphylococcus aureus | Moraxella catarrhalis |
| Unidentified Gram negative bacteria | | Streptococcus species | Coagulase-negative Staphylococcus (CNS) |
| Stenotrophomonas maltophilia | | Enterococcus species | CDT |

Figure 2:
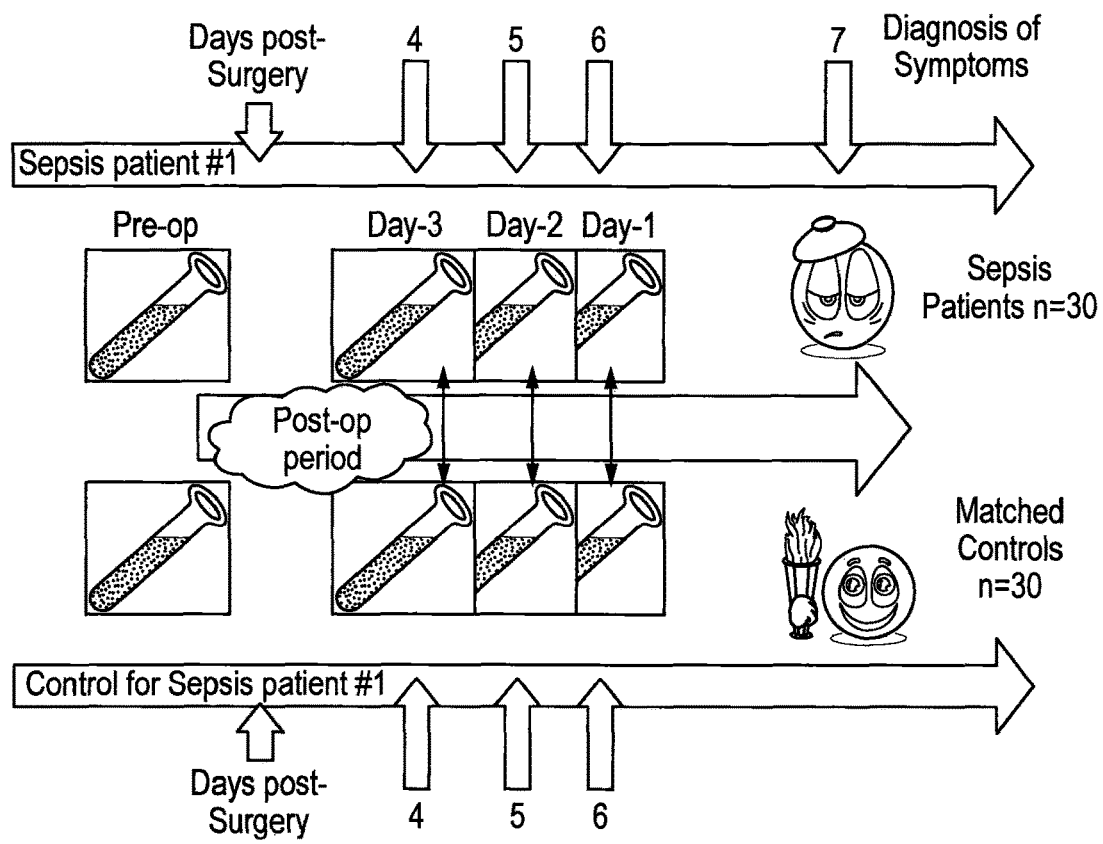
FIG. 2 is an illustration depicting the rationale for sample selection, and especially the selection of control samples, and the matching with sepsis patient samples.

Once patients were confirmed as septic, a comparator group was selected that matched each sepsis patient's age, sex and procedure. These patients did not develop SIRS as a result of their surgery. Having regard to FIG. 2, the rationale for comparator selection is illustrated as well as which patient samples were analysed and how the time frames for patient samples that are taken at different days post-surgery were standardized. It should be noted that the main analytical effort was focused on the 3 days prior to the diagnosis of sepsis as these are most likely to yield useful pre-symptomatic biomarker, signatures. The time course of the development of sepsis in a patient is indicated by the Sepsis patient #1 bar. From the large number of patients who do not go on to develop sepsis following surgery a suitable age/sex/procedure matched control is identified and used as a comparator. In this example the day of diagnosis of sepsis is day 7 post-infection. Therefore the 3 days before sepsis diagnosis are days 4, 5 and 6 post-surgery. In terms of pre-symptomatic diagnosis this may also be noted as Days −3, −2 and −1. In order to provide a robust and relevant post-operative comparison for each of the 3 days before sepsis diagnosis, the equivalent post-operative blood sample was used. In this case the blood samples taken from days 4, 5 and 6 post surgery were used for comparison, acting as Day −3, −2 and −1 controls. The process of matching the pre-symptomatic blood samples of patients who went on to develop sepsis with their most appropriate post-operative comparators was then repeated in Phase I and II of the study so that the time courses of 30 and 40 patients who go on to develop sepsis were compared to 30 and 40 post-operative comparator patients, respectively.

In addition to the non-sepsis comparator group, further controls were provided through exploitation of each patient's pre-operative sample as well as samples from patients that developed SIRS and not sepsis. This ensured that any changes observed in the transcriptomes of sepsis patients were a direct result of infection acquired during surgery. A summary of patients used in both phase I and II of the study is given in table 8. It should be noted that antibiotic use was dictated on a case-by case basis and under the discretion of the clinician. The study protocol did not influence patient management; ethically we were unable to dictate medical countermeasure use during this study.

TABLE 8

Summary of patient ages, gender, delay for sepsis and types of surgery used in phase I and II

|  | Phase I (Discovery) | | Phase II (Validation) | |
| --- | --- | --- | --- | --- |
|  | Sepsis n = 30 | Controls n = 30 | Sepsis n = 40 | Controls n = 40 |
| Age | 63 [48-81] | 61 [52-79] | 64 [28-79] | 64 [24-80] |
| Gender (female/male) | 14/16 | 14/16 | 11/29 | 11/29 |
| Delay for sepsis | 3.5 [1-8] | NA | 4.75 [1-9] | NA |
| Surgery Type | Thoracic or abdominal | Thoracic or abdominal | Thoracic, abdominal or maxillofacial | Thoracic, abdominal or maxillofacial |

Microarray Analysis (Phase I Biomarker Discovery)—

Illumina® Human HT12v4 Beadarrays were run on the samples from the 60 phase I patients (30×sepsis & 30×comparator), 80 phase II patients (40×sepsis & 40×comparator) and 40 Phase II SIRS patients. This corresponded to 192 transcriptomes analysed during Phase I and 433 transcriptomes analysed during phase II of the study. Data were collected for 30 sepsis patients and 30 age, sex and surgery matched controls (or baselines). Microarray data were collected from 192 blood samples. These represented 4 different time points corresponding to pre-operation and 1, 2 and 3 days prior to the onset of sepsis. Samples were taken for each paired baseliner based on the corresponding day of onset for the sepsis sample, summarized in table 9.

TABLE 9

The number of samples used during Phase I of the study.

|  | Comparator | Sepsis |
| --- | --- | --- |
| Pre-op | 30 | 30 |
| Onset Day −1 | 30 | 30 |
| Onset Day −2 | 21 | 21 |
| Onset Day −3 | 15 | 15 |

The Illumina® Human v4 chip contains 48,804 probes mapping to over 27,000 reference sequence numbers. Each probe is 50 base pairs long providing a high degree of specificity for each gene. For each sample globin-reduced RNA (GlobinClear™, Life Technologies, USA) was prepared from total RNA. RNA integrity was measured using a Bioanalyzer 2100 (Agilent, USA) and concentration was assessed using a NanoQuant™ (Tecan, USA). cRNA was prepared by amplification and labelling using the Illumina® TotalPrep™ RNA Amplification Kit (Life Technologies) and hybridized to Human HT-12 v4 Beadarrays USA). The Illumina® HighScanHQ™ then imaged each chip with resulting intensities indicating the expression level of each probe's corresponding gene. Background subtracted data was then generated using GenomeStudio™ Software (Illumina®, USA).

A variety of preliminary or exploratory analyses on the microarray data for Phase I were undertaken to determine whether:

1. There were any batch processing effects on the data.
2. There was a difference between pre- and post-surgical transcriptomes.
3. There was a gross difference between the transcriptomes of patients who went on to develop sepsis and their baseliner comparators.

Batch Effects

3D Principal Component Analyses (PCA) was used to examine whether the day of hybridization of sample had an impact on the transcriptomes of patients in the study.

The data indicated that samples hybridized on different days did not segregate into distinct groups. This suggested that there was no batch effect amongst the samples according to day of hybridization.

Pre- and Post-Surgical Transcriptomes

3D PCA was also used to indicate whether there were any differences in the transcriptomes of pre- and post-surgery patients. The analysis indicated that the transcriptomes of pre-surgery patients cluster together. This suggests that they are more similar to each other than to the transcriptomes of post-surgery patients. Additionally, the transcriptomes of the entire post-surgery patient samples cluster away from the pre-surgery transcriptomes, suggesting that they too have more in common with each other than with the transcriptomes of pre-surgery patients.

Differences Between Patients Who go on to Develop Sepsis and their Comparators

Like PCA, Hierarchical Clustering is a tool used for unsupervised analysis of data sets. It was used to describe the transcriptomes of both patient groups through use of a heat map. Hierarchical clustering involves the re-ordering of genes in the dataset so that similar transcriptome patterns (expression profiles) are put next to each other. In effect it is a tool that helps identify samples that are related to each other.

Preliminary inspection of the heat map indicated that the pre-surgery samples as well as the transcriptomes of baseliner patients on comparative Days −1, −2 and −3 are clustered near each other, generally at the top half of the heat map. In contrast the transcriptomes of patients who go on to develop on Days −1, −2 and −3 seem to cluster near each other near the bottom of the heat map. This suggests that there is a difference in the transcriptomes of patients who go on to develop sepsis and their baseliner comparators.

Following the collection of transcriptomic data from 192 samples, further analysis was required to elucidate key biomarkers whose expression was significantly different between the two patient groups. These host response genes would form the basis of a biomarker signature that could be used to indicate an individual who was likely to develop the symptoms associated with life-threatening disease.

Biomarker Discovery—Microarray (Phase I)—

Data Pre-Processing

There were three main steps in the data pre-processing:
1. Log transform—a $\log_e$ transform was performed on the transcriptomic data to comply with assumptions of normality required for further analysis
2. Pre-surgery subtraction—in order to obtain the log expression for each sample due to the response to surgery, all samples were normalised to the difference compared with pre-surgery expression levels.
3. Median subtraction—This was important within each gene probe to account for systematic variation.

Multiple Hypothesis Testing for Determination of Genes of Interest

We used multiple t-tests to discern evidence for significant differences in gene expression (below the threshold p-value assigned), for the 3 days before sepsis diagnosis. The analyses indicated that 452 genes were significantly different between the two patient groups on all 3 days before sepsis diagnosis. We also determined that there was evidence for significant differences between the two groups on each day before sepsis diagnosis. The expression of 91, 1022 and 938 genes had evidence for significant differential on Days 3, 2 and 1 before sepsis diagnosis, respectively.

We then took a similar approach implementing the significance analysis of microarray (SAM) analysis method (Tusher V G, Tibshirani R, Chu, X. 2001. Significance analysis of microarrays applied to the ionizing radiation response. Proc Nat Am Sci 98:5116-5121) as published by R. Tibshiriani at Stanford University. This method is commonly used for microarray analysis. We felt this alternative was worth exploring since they were likely to provide an independent validation of the first findings and therefore confidence in the eventual selection of biomarkers for pre-symptomatic diagnosis.

Expression Analysis and Subsequent SAM

Expression analysis was used as a test for the difference in gene expression between groups of subjects based on a known response variable, such as the onset of sepsis. Response variables were generated for 4 different tests, defined using the patient groups in Table 10.

TABLE 10

Patient categories used for expression analysis

| | Comparator | Sepsis |
|---|---|---|
| Onset Day −1 | B1 | S1 |
| Onset Day −2 | B2 | S2 |
| Onset Day −3 | B3 | S3 |

The four tests were:
1. S1+S2+S3 vs. B1+B2+B3
2. S1 vs. B1+B2+B3
3. S2 vs. B1+B2+B3
4. S3 vs. B1+B2+B3

The SAM package in the R statistical language software was used to perform the expression analysis for each of the 4 tests described above. For each gene i an expression statistic d is calculated from the average difference in the expression between the two response groups. This average different r is scaled by the standard deviation s, according to the following equation:

$$d_i = \frac{r_i}{s_i - s_0} : i = 1, 2, \ldots p$$

This statistic has a natural ordering based on magnitude as it measures the strength of the relationship between gene expression and the response variable.

In order to determine which genes are significantly expressed, SAM uses permutation analysis to estimate the local false discovery rate (FDR) at a variety of different test statistic thresholds (delta).

The FDR is fixed at 1% for each test to ensure a consistent risk of falsely identifying significant genes. However, the change in FDR as the threshold changes is dependent on the distribution of expression statistics, and there is often a minimum FDR for any given range of Delta.

For example, Table 11 shows the estimated false discovery rate for the diagnosis of sepsis 2 days prior to onset of symptoms.

TABLE 11

$90^{th}$ Percentile for the estimated false discovery rate for range of delta values for sepsis at Day −2.

| delta | number of genes called | 90th % FDR |
|---|---|---|
| 1.4 | 158 | 0.015927 |
| 1.41 | 145 | 0.016795 |
| 1.42 | 139 | 0.01752 |
| 1.43 | 129 | 0.013215 |
| 1.44 | 123 | 0.0132 |
| 1.45 | 118 | 0.013759 |
| 1.46 | 114 | 0.007833 |
| 1.47 | 109 | 0.007448 |
| 1.48 | 86 | 0.009439 |
| 1.49 | 75 | 0.010824 |
| 1.5 | 72 | 0.011275 |

The $90^{th}$ percentile is used as an upper bound on the likely false discovery rate (FDR). A FDR of 1% (0.01) was deemed an acceptable risk but it is clear from the above table that this increases again as we increase the delta beyond 1.47. Since this also satisfies the FDR<1% delta of 1.47 was chosen to identify 109 significant genes in total for this diagnosis.

As a consequence of this approach we identified 458 genes whose expression was different between the 2 patient groups for all 3 days prior to the onset of sepsis. In addition the expression of 167, 179 and 226 genes was found to be specifically differentially expressed between the patient groups on Days −3, −2 and −1, respectively. Unique to this test, were 163 of the total number of genes, 18 for Day−1, 12 for Day−2, and 51 for Day−3.

Models

Any biomarkers selected for further validation must be mathematically modelled so that their performance can be assessed both qualitatively and quantitatively. It is however important to determine a useful model by:

ensuring any assumptions are fit for the purpose of the analysis, determining precedent for the choice of model, unless the analysis is a new approach, undertaking an appropriate sensitivity analysis to determine the limitations of the model, correlating the model itself with scientific rationale.

Within the field of biostatistics and bioinformatics, there are many analysis pathways and algorithms (or models) available. It would be impossible to use all of these approaches to help select and validate the most appropriate biomarkers for pre-symptomatic diagnosis of sepsis. In the context of this project the criteria for the analyses used is described in Table 12, where a number of approaches are gradually discounted due to likely model requirements.

TABLE 12

Down-selection of models used for biomarker selection and analysis.

| Model Requirements | Potential Models |
|---|---|
| Data are non linear (shown in Lukaszewski et al. 2008) | Kernal based PCA, Support Vector Machines (SVM), Quadratic regression, Decision Trees, Random Forests, Artificial Neural Networks (ANN), Quadratic Discriminant Analysis (QDA), Naive Bayes classifier, K-Nearest Neighbour Analysis (KNN) and Factor analysis. |
| Solution needs to be resolved quickly | Kernal based PCA, SVM, Quadratic regression, Random Forests, ANN, QDA, Bayes classifier, KNN, factor analysis. |
| Due to potential use, model needs to learn and adapt to new variation in data. | From list above, quadratic regression, factor analysis and KNN will not fit this criterion. |
| Provide a classification. What's left? | PCA will not provide a classification algorithm, generally used for exploratory analysis. SVM, Decision Tress, Random Forests, ANN, QDA and Bayes classifier |

Several models were generated to determine the best fit.

Analysis 1

Support vector machines (SVMs), Random Forests and Differential analysis were used to identify genes for down selection for targeted qRT-PCR on the Fluidigm array. Survival analysis, which makes use of longitudinal information, was also used. All analysis was carried via R 2.14.0 and relevant R packages.

SVMs and random forests are supervised machine learning algorithms commonly used as bioinformatic tools. The ease of variable (gene) selection provided by these methods was a key factor in adoption of the methods. A SVM uses observations to find a hyper-plane that best separates two labelled groups. The Random Forest algorithm is an ensemble classifier, which uses bagging to create many independent classification trees. Each tree has its own training dataset, a subset of original observations is approximately 66% of the samples, with the remaining samples used to determine that tree's accuracy. Each classification tree was created using a random subset of variables allowing genes to be ranked based on a measure of how strongly they influence tree accuracies called the mean Gini coefficient. Random forests are probabilistic classifiers yielding a value between 0 and 1 indicating the probability that a given sample belongs to a particular class.

Survival analysis was also employed to find probes that play a role in the development of sepsis. The method's main attraction is that it allows microarray data from different days to be incorporated in to the model whereas the machine learning approaches use only one point to find important genes. However, the technique was not developed for prediction and creates a separate model for each gene. Similar to the t-statistic from standard differential expression, a test statistic is computed for each gene that is then used to rank genes.

The SVM, Random Forest, differential expression, and survival analysis approaches showed significant overlap in gene selection when analysing Phase I microarray data, as detailed in Table 13. The top 531 genes prior to sepsis found by random forest and SVM and survival analysis using all post operation time samples overlapped greatly with genes found by differentially expressed genes. All overlaps were highly significant (p-value <0.001) and the numbers of overlapping genes are given in Table 13.

TABLE 13

Differential expression analysis of expressed genes - overlapping genes between different models.

| Method | SVM | Survival Analysis | Differential Expression |
|---|---|---|---|
| Random Forest | 154 | 140 | 59 |
| SVM |  | 255 | 98 |
| Survival Analysis |  |  | 91 |

Prediction rates using this data were then calculated through Random forests and support vector machines (SVMs). Individual days (pre-op, day−1, etc.) were split into sepsis and control. For day−1, day−2, and day−3 predictions were made with pre-op normalization by division, by subtraction, and without normalization. Averages across days were also considered, for example day−1 and day−2 averaged for each patient. In order to maintain the assumption that samples were independent, no days were grouped together into a meta group (in either sepsis or control). For survival analysis all data were used under the false assumption that each time point was equally spaced (time between pre-op and day−3 was variable).

Random Forest Prediction of Sepsis

Random forests are composed of many simple tree classifiers, each based on a different random subset of samples for training and testing each tree (70% vs. 30%) thus allowing for accurate estimates of error rates. Below are the sensitivity and specificity for predicting sepsis in each time grouping. Note that Day −2 and Day −3 (D−2 and D−3) have smaller sample sizes. Normalizing by pre-op (by division of unlogged data) and combining days showed that averaging Days −1 and 2 yields the most accurate results. Normalization by subtraction (not shown) performed no better than normalization by division.

TABLE 14

Performance of identified genes using Random Forests

| Filtered | Sensitivity | Specificity | Error Rate |
|---|---|---|---|
| Pre-op | 0.667 | 0.643 | 0.345 |
| D-3 | 0.786 | 0.8 | 0.207 |
| D-2 | 0.95 | 0.857 | 0.0976 |
| D-1 | 0.778 | 0.786 | 0.218 |

To provide a comparison to random forests a Support Vector Machine (SVM) with, a Wilcoxon test to allow for non-normally distributed probes was employed (Table 15). We concentrated on the Day-1 and Day-2 average given that this performed the best and used 5 fold cross validation using 20% for testing. Standard errors are shown in parentheses.

TABLE 15

Performance of identified genes using Support Vector Machines.

| | Sensitivity | Specificity | Error Rate |
|---|---|---|---|
| D-1n2 ave | 0.8 (0.082) | 0.69 (0.027) | 0.253 (0.044) |
| D-1n2 ave Filtered | 0.853 (0.037) | 0.807 (0.11) | 0.164 (0.06) |

Both approaches demonstrated acceptable, but not outstanding, differentiations between the two patient groups. This suggested that other techniques may be useful when trying to model these datasets.

Analysis 2

Artificial Neural networks (ANNs) provide the ability to predict classes of data given an unknown pattern in a set of example data, and have been used successfully in a pilot study. The neural network analysis is described by the following process. This was performed separately 5 times to show possible changes in predictive ability.

1. Gene expression data was identified based on SAM analysis for each separate test, all sepsis, sepsis Day -1, -2 and -3. This data was normalized by subtracting the median and scaling by the standard deviation for each gene.
2. Normalized data was split into 70% subset used for training and 30% used for validating the neural network
3. The neural network was trained and weights for each hidden unit are used to form a predictor for new data.
4. The 30% subset was passed through the predictor and a probability is given for assignment to each of the two groups. (Sepsis, Non-sepsis)
5. The predictive ability of the neural network was based on specificity and sensitivity estimated from the 30% unknown data set.

An average specificity and sensitivity was then gained from the five separate neural networks and the results are summarized in Table 16.

TABLE 16

Summary results for prediction of sepsis on different days with intervals based on standard error of the five repeated predictors, as based on the genes identified by SAM analysis.

| Test | Sensitivity | Standard Deviation (+/−) | Specificity | Standard Deviation (+/−) |
|---|---|---|---|---|
| sepsis on any day | 89.7% | 7.4% | 89.4% | 7.2% |
| sepsis on Day -1 | 70.8% | 11.8% | 91.6% | 3.3% |
| sepsis on Day -2 | 73.4% | 12.7% | 93.5% | 5.4% |
| sepsis on Day -3 | 72.8% | 13.0% | 94.7% | 6.5% |

Neural network analysis is restricted by the number of samples which can be used to estimate the sensitivity/specificity since new data must be passed through the predictor. We fully accept that with this data set, other classification techniques may be able to provide more accurate results based on larger number of patients. However, it did perform better than the techniques used in Analysis 1.

Having regard to the 458 genes identified in the SAM analysis, and due to the natural ordering of the magnitude of the test statistic, it was possible to select genes from the top of this list in order to find a smaller subset with a similar predictive ability (data not shown).

As a consequence of the different analyses conducted in Analysis 1 and Analysis 2, a down select of biomarkers was conducted. Those biomarkers identified as most predictive by any of the techniques outlined above were selected to be taken forward for further analysis using the Fluidigm q RT-PCR array system. In total 270 genes were selected along with 6 housekeeping genes (BRD7, PWWP2A, RANBP3, TERF2, SCMH1, FAM105B) selected based on consistent expression across all samples.

Fluidigm Confirmation and Quantitation of Microarray Biomarkers—

The Fluidigm BioMarkHD was used to profile 270 genes in the 60 phase I and 80 phase II samples taken at all time points. The BioMarkHD™ is a qPCR assay that runs 96 primer-probe pairs in 96 samples. Specifically, globin-reduced RNA (GlobinClear™, Life Technologies, USA) was converted to cDNA (High Capacity RT kit, Life Technologies, USA) and preamplified by limited PCR (PreAmp™ Master Mix, Life Technologies, USA) with a pool of primers (DeltaGene, Fluidigm, USA) for all assays of interest (in this case, a pool of 276 assay primer pairs). Preamplified cDNAs were treated with Exonuclease I (New England Biolabs, USA) and diluted to remove unused primers and dNTPs and to prepare samples for qPCR. Preamplified samples were combined with 2× SsoFast EvaGreen Supermix with Low ROX (Bio-Rad, USA) and 20×DNA Binding Dye Sample Loading Reagent (Fluidigm, USA) and assays (primer pairs) were combined with 2× Assay Loading Reagent (Fluidigm, USA). Samples and Assay mixes were loaded onto a 96 by 96 Dynamic Array IFC for real-time PCR analysis on a BioMarkHD™ (Fluidigm, USA). Pre-processing was performed, using Fluidigm's Real Time PCR Analysis Software to determine cycle threshold (Ct) values, using linear (derivative) baseline correction and auto-detected, assay-specific threshold determination. Reference or housekeeping genes are used to normalize each assay and produce delta Ct values. Reference samples are then used to normalize all samples on the plate with resulting values referred to as a delta-delta Ct's. Three 96 by 96 plates were used to profile all 270 genes plus 0.6 housekeeping genes on each plate.

A total of 269 (the original Phase I 192+extra samples from the comparator group) samples from the 60 phase I patients and 439 samples from the 80 Phase II patients (+40

SIRS patient samples) were profiled via the Fluidigm Bio-Mark™. It should be noted that data from Phase I of the study was first analysed. The initial analysis used SVM to assess the performance of the down-selected biomarker list. The array was very good at identifying non-sepsis comparator patients, as detailed in Table 17. However, its performance for positive identification of sepsis patients diminished with time from sepsis diagnosis. Furthermore, when the data for the three days prior to sepsis is pooled, the array gave an overall predictive accuracy of 78.8%.

TABLE 17

Performance (%) of down-selected biomarkers in prediction of pre-symptomatic sepsis patients and their comparators on Phase I data using the Fluidigm array

| | Comparator | | Sepsis | |
|---|---|---|---|---|
| | No. of patients | % Predictive Accuracy | No. of patients | % Predictive Accuracy |
| DAY −1 | 29 | 100 | 30 | 90 |
| DAY −2 | 25 | 100 | 21 | 71.4 |
| DAY −3 | 22 | 100 | 15 | 66.67 |
| DAY −4 | 20 | 95 | 11 | 54.5 |

TABLE 18

45 and 25 gene classifiers whose predictive accuracy was tested in Phase II of the study using microarray and Fluidigm array analysis of 433 blinded RNA samples.

| 45 Gene Classifier | 25 Gene Classifier |
|---|---|
| ATP9A, C16ORF7, C5ORF39, C9ORF103, CACNA1E, CD177, DHRS3, EEF1B2, FCER1A, FLT3LG, GAS7, GRB10, HLA.DMA, HS.445036, IL1R1, IL1R2, LOC285176, MYBPC3, NCOA3, NDST2, RPL10A, EBI2, LOC646483, RPL13A, RPL18, RPL18A, RPL32, RPL36, RPL9, RPS20, RPS29, RPS6, SIGIRR, SLBP, SLC26A6, SMPDL3A, SORBS3, TCEA3, TCTN1, THBS3, THNSL1, TIMM9, TOMM7, ZFAND1, ZNHIT3 | C16ORF7, C5ORF39, C9ORF103, CD177, FCER1A, GAS7, LOC285176, MYBPC3, NDST2, EBI2, RPL13A, RPL18A, RPL32, RPL36, RPL9, RPS20, RPS29, RPS6, SIGIRR, TCEA3, TCTN1, TIMM9, TOMM7, ZFAND1, ZNHIT3 |

We made predictions as to the type of patient that each sample had come from and sent them to be unblended. The performance of these classifiers is summarised in Table 19.

TABLE 19

Performance (%) of biomarker classifiers -
(A) predictive accuracies for samples from Comparator patients,
(B) predictive accuracies for samples from pre-symptomatic sepsis patients

| | Number of patients | Equivalent Day Pre-SEPSIS Diagnosis | Microarray SepClass 25 Genes | Microarray SepClass 45 Genes | Fluidigm SepClass 25 Genes | Fluidigm SepClass 45 Genes |
|---|---|---|---|---|---|---|
| A | | | | | | |
| CONTROL | 34 | DAY −1 | 91.2 | 91.2 | 61.8 | 82.4 |
| CONTROL | 30 | DAY −2 | 86.7 | 86.7 | 60.0 | 76.7 |
| CONTROL | 27 | DAY −3 | 88.9 | 88.9 | 63.0 | 74.1 |
| CONTROL | 22 | DAY −4 | 81.8 | 81.8 | 63.6 | 72.7 |
| B | | | | | | |
| SEPSIS | 37 | DAY −1 | 64.9 | 64.9 | 91.9 | 75.7 |
| SEPSIS | 31 | DAY −2 | 71.0 | 71.0 | 90.3 | 80.6 |
| SEPSIS | 28 | DAY −3 | 67.9 | 67.9 | 92.9 | 78.6 |
| SEPSIS | 21 | DAY −4 | 81.0 | 81.0 | 95.2 | 76.2 |

Optimising the Biomarker Signature

Due to the performance of the classifiers within Phase 1, it was decided that the biomarker list required updating in the light of new knowledge. The results from Phase 1 enabled down selection of the gene list based on differential analysis.

Biomarker Validation with Phase II Samples—Blind Testing with Independent Data Sets.

A fresh set of patient samples were obtained over the course of the study and used to validate the down-selected genes from Phase I, All RNA samples were prepared, blinded and sent for analysis using microarray and Fluidigm array analysis, 266 genes were determined through several methods such as using SAM analysis, as mentioned above. This gene set was then further reduced through the use of measures taken from the classifying algorithms used, such as the Gini coefficient in the random forest classifier.

Two groups of classifiers were then selected, one with 45 genes, and the other 25 genes. These are indicated in Table 18.

Table 19 demonstrates that the analysis undertaken can classify to a given level between sepsis patients and non-sepsis patients and their comparators. The tables also show that the further away from the day of sepsis diagnosis and as the N reduces, the classifier performance increases.

Biomarker Assessment—

Following the decision to remove some of the biomarkers from the original Fluidigm array, we re-constituted 31.5% of them with more candidate biomarkers identified for Phase II with more candidates. This final list of biomarkers still held the 180 highly significant genes identified and used for Fluidigm validation during Phase I. Additional candidate biomarkers identified by SAM analysis, were added to increase the likelihood of finding key pre-symptomatic biomarkers. This then enabled the gene list to keep what was determined as optimum genes and add in other genes into the list that the differential analysis showed as significant. This final list is listed in Table 20.

TABLE 20

Final Down-Selected genes for use on Fluidigm array during Phase II

| | | | | | | |
|---|---|---|---|---|---|---|
| ACTR6 | EBI2 | CXORF42 | SORBS3 | RPL11 | SLC26A8 | ATP2A2 |
| BIN1 | GAS7 | CLASP1 | TIMM9 | PPP2R2B | WDR37 | ZNF608 |
| C16ORF7 | HIST2H4B | CD2 | TST | NOL11 | ZNF17 | TBC1D8 |
| CD247 | IL1R1 | C14ORF112 | CCDC65 | GZMK | ANKS1A | RRBP1 |
| CLNS1A | LGALS2 | BCL6 | NCOA3 | ZNF32 | CD59 | RPL26 |
| CYB561 | LTA | MRPL24 | PDCD4 | TMEM42 | EIF3D | PHCA |
| FCER1A | EEF1B2 | LOC646483 | RASGRP1 | TCEA3 | GYG1 | NSUN7 |
| GRB10 | CTSS | KLRG1 | RPL18A | SLC2A11 | KIF1B | LETMD1 |
| HS.445036 | CD7 | HLA-DRA | RPS14 | SERTAD2 | MMP9 | IRAK3 |
| LARP5 | CACNA1E | GRAMD4 | RPS6 | RPS20 | PAG1 | FAM160A2 |
| LOC646766 | C12ORF57 | MRPS6 | SIVA | RPL38 | RPL19 | CTDP1 |
| MRPL50 | AOC2 | OLFML2B | SS18L2 | RPL12 | RPS15 | ATP8B4 |
| ADRB2 | LY6E | PTPRCAP | TMC6 | PRKCQ | SLC36A1 | RPS3A |
| BOAT | LOC285176 | RPL13 | TTLL3 | OLFM1 | WWP1 | TDRD9 |
| C21ORF7 | IL1R2 | RPL7A | CDO1 | HLA-DRB3 | ARG1 | RUNX1 |
| CD3D | HLA-DMA | RPS27 | RPSA | ZNF430 | CKAP4 | RPL27A |
| CPA3 | GBP1 | SH2D1A | RPS15A | TOMM7 | EMILIN2 | PHTF1 |
| DHRS3 | EOMES | SMAD2 | RPL30 | TCTN1 | HIBADH | NT5DC2 |
| FLT3LG | CUTL1 | THBS3 | RCN2 | SLC38A10 | MUC1 | LOC153561 |
| GTPBP8 | CD96 | TP53BP2 | PECI | ACVR1B | PFKFB2 | ITGAM |
| ICAM2 | CCL5 | ZNHIT3 | NDST2 | C13ORF23 | RPL22 | FBXO34 |
| LDHA | C12ORF62 | LEPROTL1 | EFCBP1 | DACH1 | RPS25 | CYP1B1 |
| LOC652071 | ASNSD1 | MS4A4A | ZFAND1 | FBXW2 | SLC41A3 | ATXN7L3 |
| MRPS27 | MAFG | P117 | TMEM150 | ITGAX | ZC3H3 | TRPM2 |
| AKR1B1 | LOC644096 | PYHIN1 | SSBP2 | LOC647099 | NAPB | RPL4 |
| BTBD11 | IL32 | RPL13A | SLBP | OPLAH | LARP4B | PLAC8 |
| C5ORF39 | HLA-DMB | RPL9 | RTP4 | PTPN1 | HIPK2 | |
| CD3E | GBP4 | RPS29 | RPS17 | RPL5 | EXOC7 | |
| CR1 | EXOSC5 | SIGIRR | RPL32 | SIL1 | CMTM4 | |
| DIP2A | CXORF20 | SMPDL3A | RPL10A | UPP1 | ARID5B | |
| GALM | CDKN2AIP | THNSL1 | POP5 | TFB1M | ZDHHC19 | |
| HDC | CD177 | TRAT1 | NMT2 | AMD1 | SORT1 | |
| ICOS | C12ORF65 | OSTALPHA | FAM26F | C22ORF9 | RPS8 | |
| LDOC1 | ATP9A | MYBPC3 | ZNF195 | DNAJC5 | RPL24 | |
| LSG1 | METTL7B | P2RY5 | TMEM204 | GOLGA1 | PGD | |
| AMPH | LOC646200 | RARRES3 | TBCC | KIAA1881 | NLRC4 | |
| C11ORF1 | ITM2A | RPL18 | SLC26A6 | MACF1 | LDLR | |
| C9ORF103 | HLA-DPA1 | RPS10 | SELM | P4HB | HK3 | |
| CD6 | GPR107 | RPS5 | RPS18 | RPL15 | EXT1 | |
| CRIP2 | FAM69A | SIRPG | RPL36 | RPS13 | CSGALNACT2 | |

In order to understand why these candidate biomarkers are indicative of sepsis in the two patient populations, the pathways and networks affected by changes in the expression of these down-selected genes were analysed using GeneGo software. The complement, epithelial to mesenchymal and cytoskeletal remodelling pathways had the highest proportion of genes that were over-expressed of all host pathways at 1 day prior to sepsis diagnosis. In contrast, pathways associated with immune cell and G protein signalling had the highest proportion of down-regulated genes of host response pathways at 1 day prior to sepsis diagnosis. The inflammatory, apoptosis and cell adhesion networks were most up-regulated in the healthy comparator patients, and consequently most down-regulated in the sepsis patient group. A similar pattern was observed for the networks controlling protein translation, antigen presentation and T cell receptor signalling.

q RT-PCR Validation of Highlighted Biomarkers—Blind Testing with Independent Data Set (Phase II Samples).

Given the performance of the first down-selected biomarker signatures, it was decided that we would also down-select a second set of biomarkers that would give good predictive accuracies with lower numbers of genes. In order to compare with the first set 2 pre-symptomatic biomarker classifiers consisting of 44 and 25 gene were down-selected by taking random samples of the 266 gene list and determining the predictive accuracy of the ANN. The 44 and 25 gene listed in Table 21 were the gene lists that enabled the highest value for predictive accuracy.

TABLE 21

44 and 25 gene classifiers whose predictive accuracy was tested in Phase II of the study using Fluidigm array analysis of 433 blinded RNA samples

| 44 Gene Classifier | 25 Gene Classifier |
|---|---|
| ACTR6, BIN1, C16ORF7, CD247, CLNS1A, CYB561, FCER1A, GRB10, HS.445036, LARP5, LOC646766, MRPL50, ADRB2, BOAT, C21ORF7 | ACTR6, BIN1, C16ORF7, CD247, CLNS1A, CYB561, FCER1A, GRB10, HS.445036, LARP5, LOC646766, MRPL50, ADRB2, BOAT, C21ORF7 |
| CD3D, CPA3, DHRS3, FLT3LG, GTPBP8, ICAM2, LDHA, LOC652071, MRPS27, AKR1B1, BTBD11, C5ORF39, CD3E, CR1, DIP2A, GALM, HDC, ICOS, LDOC1, LSG1, AMPH, C11ORF1, C9ORF103, CD6, CRIP2, EBI2, GAS7, HIST2H4B, IL1R1 | CD3D, CPA3, DHRS3, FLT3LG, GTPBP8, ICAM2, LDHA, LOC652071, MRPS27, AKR1B1 |

Exploratory Analysis

Principal component analysis (PCA) was performed for sepsis, SIRS and comparator patient data using 266 genes on the validation cohort. The separation of the three groups of patients allowed further analysis to be undertaken as it demonstrated that there was a separation between the groups to be found by the classification algorithms. This separation was made more noticeable when PCA analysis, using the DstI 44 gene classifier, was used on the validation cohort.

ANN Results

The ANN approach undertaken has already been described as part of the Phase I work. The training and testing (70:30) was undertaken using data/samples taken from 70 sepsis patients and 70 comparators (combination of phase 1 and phase 2 patients), at different time points corresponding to pre-operation, and 1, 2, and 3 days prior to the onset of sepsis, and thus using over 600 samples. Summary results for prediction of sepsis on different days with intervals based on standard error of the five repeated predictors are shown in Table 22, using the artificial neural network detailed in Table 2.

TABLE 22

Summary results for prediction of sepsis through use of an ANN.

| Test (no. of genes) | Predictive Accuracy | Standard Deviation (+/−) | Sensitivity | Standard Deviation (+/−) | Specificity | Standard Deviation (+/−) |
|---|---|---|---|---|---|---|
| 266 | 95.02% | 3.9303% | 4.7124% | 5.3014% | 5.5714% | 3.0000% |
| 44 | 97.24% | 1.4046% | 1.7348% | 1.0897% | 4.4074% | 2.4856% |
| 25 | 92.00% | 3.7202% | 9.3839% | 8.7481% | 8.2601% | 4.2226% |

The results demonstrate that the ANN can classify sepsis and non-sepsis patients to a high degree of confidence. This confidence shows little variation when reducing the number of genes in the classifier, for example to 25. The results also suggest that there is an optimal number of genes on which to classify.

Neural Network Analysis—SIRS

A potential confounder for these results is the possibility that the biomarker signature of patients who develop SIRS but NOT sepsis is similar to or overlaps with those for sepsis patients. This could give rise to false positives and undermine the predictive value of the pre-symptomatic biomarker signature for sepsis. This would lead to a lack of confidence in the findings. For this reason, data for 40 SIRS patients were run through the ANN against the sepsis biomarker signature, the results of which are shown in Table 23.

TABLE 23

Summary results for prediction of sepsis vs. SIRS on different days with intervals, based on standard error of the five repeated predictors

| Test (no. of genes) | Predictive Accuracy | Standard Deviation (+/−) | Sensitivity | Standard Deviation (+/−) (+/−) | Specificity | Standard Deviation (+/−) (+/−) |
|---|---|---|---|---|---|---|
| 266 | 95.22% | 10.25% | 0.2 | 0.447214 | 0.002 | 0.004472 |
| 44 | 100.00% | 0.00% | 0 | 0 | 0 | 0 |
| 25 | 99.84% | 0.36% | 0 | 0 | 0.001961 | 0.004384 |

The results in Table 23 show that the ANN effectively classifies between sepsis and SIRS patient biomarker signatures. Again as with Table 22, there appears to be an optimum number of genes for the classification. Furthermore the difference between results for 263 genes and 45 genes suggests that the 263 gene biomarker list does have a commonality with the SIRS signature within it.

Through the production of 44,014 combinations/biomarker signatures of 44 biomarkers, randomly selected from the list of 266, it has been shown that all combinations have a mean predictive accuracy of greater than 75% (in fact above 76.1%). The abundance of individual genes in the top and bottom 1000 subsets is not uniform; the genes which appear more frequently in the top subsets of 44, appear less frequently in the bottom subsets, and vice versa.

Figure 3:
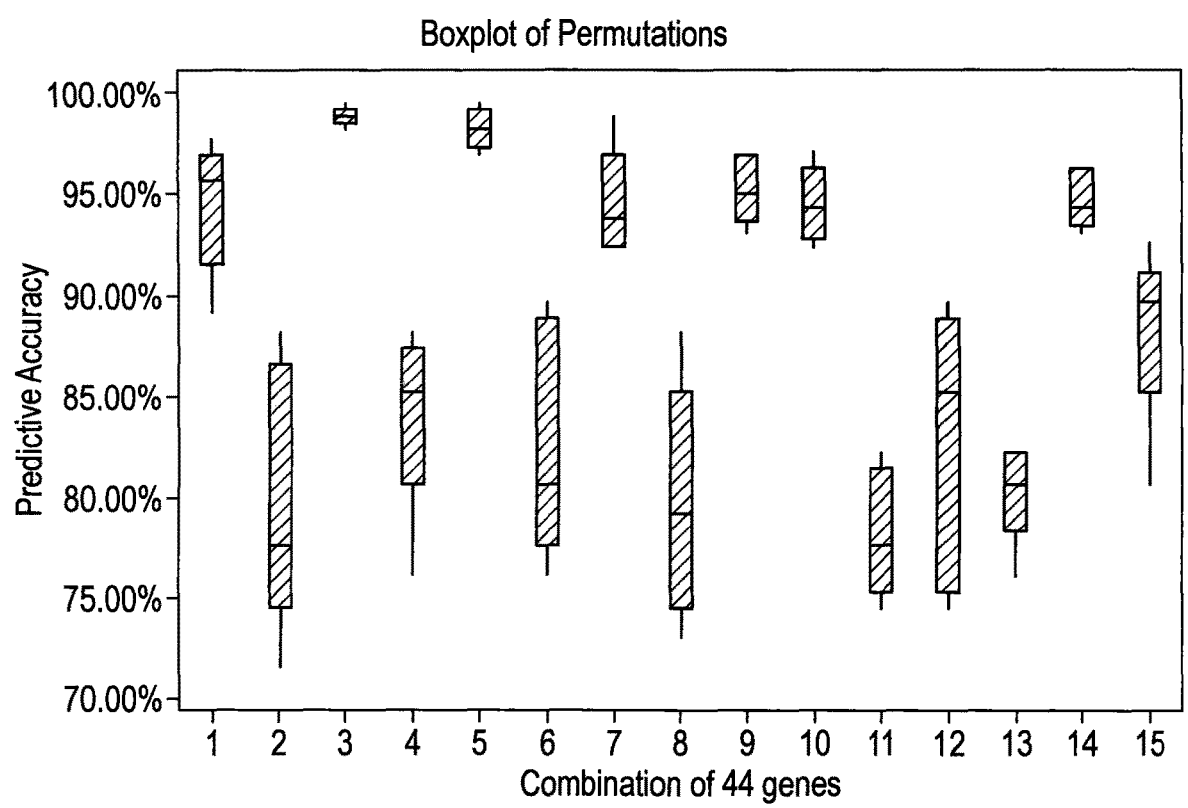
FIG. 3 is a graph detailing the predictive accuracies for sepsis versus non-sepsis of the combinations detailed in Table 24.

These results are illustrated by the 15 specific combinations listed in Table 24, which have the accuracies shown in FIG. 3. Thus in one embodiment the biomarker signature comprises at least 44 genes selected from the list of genes consisting of the 266 genes listed in Table 1.

TABLE 24

Fifteen combinations of 44 biomarkers tested for predictive accuracies. The predictive accuracies are illustrated in FIG. 3.

| 1 | 2 | 3 | 4 | 5 | 6 | 7 | 8 |
|---|---|---|---|---|---|---|---|
| CYB561 | BIN1 | ACTR6 | BOAT | ACTR6 | BIN1 | C16ORF7 | CYB561 |
| GRB10 | FCER1A | BIN1 | LOC652071 | BIN1 | ADRB2 | LARP5 | FCER1A |
| BTBD11 | LOC646766 | LOC646766 | DIP2A | C16ORF7 | BOAT | C21ORF7 | MRPL50 |
| CD3E | MRPL50 | ICAM2 | C11ORF1 | CD247 | FLT3LG | GTPBP8 | ADRB2 |
| EBI2 | ADRB2 | LOC652071 | CD6 | CLNS1A | LOC652071 | LDHA | LOC652071 |
| CD7 | CD3E | ICOS | HIST2H4B | CYB561 | CR1 | MRPS27 | ICOS |
| LOC285176 | CACNA1E | CD7 | EEF1B2 | FCER1A | DIP2A | BTBD11 | AMPH |
| HLA-DMA | AOC2 | IL1R2 | C12ORF57 | GRB10 | LY6E | HDC | C9ORF103 |
| C12ORF62 | LY6E | ASNSD1 | IL1R2 | HS.445036 | HLA-DMA | CRIP2 | C12ORF57 |
| ASNSD1 | GBP4 | MAFG | CXORF20 | LARP5 | GBP1 | IL1R1 | AOC2 |
| GPR107 | CDKN2AIP | GBP4 | CD177 | LOC646766 | MAFG | CACNA1E | HLA-DMA |
| BCL6 | METTL7B | CXORF20 | CD2 | MRPL50 | LOC644096 | LOC285176 | CDKN2AIP |
| MRPL24 | HLA-DPA1 | HLA-DPA1 | BCL6 | ADRB2 | ATP9A | HLA-DMA | C12ORF65 |
| RPL7A | LOC646483 | CXORF42 | LOC646483 | BOAT | CLASP1 | ASNSD1 | ATP9A |
| RPL13A | MRPS6 | MRPL24 | HLA-DRA | C21ORF7 | BCL6 | LOC644096 | LOC646200 |
| RPS5 | OLFML2B | PTPRCAP | PTPRCAP | CD3D | RPL7A | IL32 | HLA-DPA1 |
| CCDC65 | SH2D1A | RPL7A | TP53BP2 | CPA3 | THBS3 | FAM69A | LOC646483 |
| NCOA3 | SIRPG | PYHIN1 | SORBS3 | DHRS3 | P2RY5 | MRPL24 | RPL7A |
| RASGRP1 | RPS14 | RASGRP1 | NCOA3 | FLT3LG | RPS5 | HLA-DRA | TP53BP2 |
| RPS6 | RPS15A | RPL30 | RPS6 | GTPBP8 | RASGRP1 | MRPS6 | ZNHIT3 |
| NMT2 | RCN2 | EFCBP1 | SS18L2 | ICAM2 | RPS14 | RPS27 | RPL13A |
| ZNF32 | EFCBP1 | TMEM150 | RPS15A | LDHA | RPSA | PYHIN1 | TRAT1 |
| SERTAD2 | NMT2 | RPL32 | ZFAND1 | LOC652071 | RPS17 | SIGIRR | P2RY5 |
| RPL38 | NOL11 | ZNF195 | RPS18 | MRPS27 | NMT2 | SMPDL3A | RARRES3 |
| SLC38A10 | ZNF32 | TMEM204 | NOL11 | AKR1B1 | SLC26A6 | P2RY5 | CCDC65 |
| ACVR1B | SLC2A11 | SELM | TMEM42 | BTBD11 | DACH1 | RARRES3 | RPS6 |
| P4HB | OLFM1 | RPS18 | RPL12 | C5ORF39 | RPL5 | TTLL3 | RPSA |
| SLC26A8 | LOC647099 | PPP2R2B | ZNF430 | CD3E | TFB1M | RPS15A | RCN2 |
| WDR37 | OPLAH | OLFM1 | SLC38A10 | CR1 | AMD1 | RPL36 | RPL32 |
| PAG1 | ZNF17 | TCTN1 | ACVR1B | DIP2A | MACF1 | TMEM42 | RPL36 |
| RPL19 | KIF1B | DACH1 | DACH1 | GALM | KIF1B | HLA-DRB3 | RPL12 |
| SLC41A3 | RPS15 | ITGAX | UPP1 | HDC | SLC36A1 | FBXW2 | OLFM1 |
| LARP4B | MUC1 | TFB1M | GOLGA1 | ICOS | WWP1 | LOC647099 | ZNF430 |
| ZDHHC19 | PFKFB2 | GYG1 | MACF1 | LDOC1 | PFKFB2 | ZNF17 | TOMM7 |
| SORT1 | NAPB | MMP9 | P4HB | LSG1 | RPS25 | CD59 | GOLGA1 |
| NLRC4 | LDLR | PAG1 | SLC36A1 | AMPH | CMTM4 | KIF1B | ZNF17 |
| EXT1 | ATP2A2 | RPS15 | CKAP4 | C11ORF1 | RPS8 | SLC36A1 | CD59 |
| ATP2A2 | RRBP1 | CKAP4 | PFKFB2 | C9ORF103 | PGD | PFKFB2 | PAG1 |
| ZNF608 | IRAK3 | RPL22 | ZC3H3 | CD6 | TBC1D8 | SLC41A3 | RPL19 |
| RRBP1 | ATP8B4 | ZDHHC19 | CMTM4 | CRIP2 | LETMD1 | EXOC7 | ZC3H3 |
| TDRD9 | PHTF1 | SORT1 | ZDHHC19 | EBI2 | IRAK3 | HK3 | NAPB |
| RUNX1 | NT5DC2 | NLRC4 | NLRC4 | GAS7 | RPS3A | ATP2A2 | HIPK2 |
| LOC153561 | LOC153561 | CSGALNACT2 | PHTF1 | HIST2H4B | PHTF1 | LETMD1 | ZNF608 |
| ITGAM | FBXO34 | RRBP1 | TRPM2 | IL1R1 | NT5DC2 | ITGAM | PHCA |

| 9 | 10 | 11 | 12 | 13 | 14 | 15 |
|---|---|---|---|---|---|---|
| CD6 | BCL6 | CUTL1 | CDKN2AIP | LOC652071 | EBI2 | AOC2 |
| CD247 | CLNS1A | GTPBP8 | CLNS1A | BIN1 | CD247 | LOC646766 |
| CLNS1A | CYB561 | LDHA | ADRB2 | CYB561 | FCER1A | BOAT |
| C5ORF39 | FCER1A | BTBD11 | FLT3LG | GRB10 | ICAM2 | DIP2A |
| GALM | C21ORF7 | ICOS | GTPBP8 | LARP5 | C5ORF39 | CRIP2 |
| ICOS | FLT3LG | C11ORF1 | IL1R1 | LOC646766 | EEF1B2 | CUTL1 |
| AOC2 | CTSS | CD6 | CD7 | DIP2A | C12ORF57 | CD96 |
| IL1R2 | CD96 | LGALS2 | CACNA1E | LSG1 | AOC2 | HLA-DMB |
| CUTL1 | CCL5 | GBP1 | GBP4 | EBI2 | EOMES | EXOSC5 |
| CDKN2AIP | HLA-DMB | ASNSD1 | EXOSC5 | EEF1B2 | IL32 | ITM2A |
| ITM2A | CDKN2AIP | CDKN2AIP | CXORF20 | CD7 | GBP4 | HLA-DPA1 |
| CLASP1 | GPR107 | ITM2A | CD177 | LY6E | CD177 | BCL6 |
| C14ORF112 | CXORF42 | C14ORF112 | METTL7B | C12ORF65 | HLA-DPA1 | MRPL24 |
| BCL6 | CLASP1 | BCL6 | HLA-DPA1 | METTL7B | C14ORF112 | LOC646483 |
| LOC646483 | RPS27 | HLA-DRA | CD2 | ITM2A | BCL6 | KLRG1 |
| RPS27 | SMAD2 | RPS29 | RPS27 | LOC646483 | MRPL24 | GRAMD4 |
| P117 | ZNHIT3 | OSTALPHA | TP53BP2 | RPS27 | RPS27 | PYHIN1 |
| RPL9 | RPL13A | TST | SIGIRR | SIGIRR | P117 | SMPDL3A |
| RPS10 | SMPDL3A | CCDC65 | OSTALPHA | TRAT1 | NCOA3 | RPS5 |
| SORBS3 | TMEM150 | NCOA3 | RARRES3 | OSTALPHA | RASGRP1 | RASGRP1 |
| TST | FAM26F | PDCD4 | SIRPG | NCOA3 | RPS6 | RPL18A |
| RPL18A | TBCC | SLBP | SORBS3 | RPL18A | PECI | RPSA |
| SS18L2 | TCEA3 | RPL10A | RPL30 | RPS15A | EFCBP1 | TMEM150 |
| CDO1 | ITGAX | GZMK | NDST2 | RCN2 | TMEM150 | ZNF195 |
| RPS15A | PTPN1 | RPL12 | SLBP | RTP4 | NMT2 | SLC26A6 |
| TMEM150 | TFB1M | PRKCQ | RTP4 | SLC2A11 | SLC26A6 | SLC2A11 |
| RPL32 | AMD1 | HLA-DRB3 | RPL11 | HLA-DRB3 | RPL11 | PRKCQ |
| SLC26A6 | KIAA1881 | OPLAH | ZNF32 | C13ORF23 | PPP2R2B | HLA-DRB3 |

TABLE 24-continued

Fifteen combinations of 44 biomarkers tested for predictive accuracies. The predictive accuracies are illustrated in FIG. 3.

| | | | | | | |
|---|---|---|---|---|---|---|
| RPS20 | CD59 | UPP1 | RPS20 | LOC647099 | ZNF32 | TCTN1 |
| HLA-DRB3 | KIF1B | KIAA1881 | HLA-DRB3 | OPLAH | ACVR1B | ITGAX |
| TCTN1 | RPL19 | P4HB | ACVR1B | ANKS1A | TFB1M | AMD1 |
| P4HB | NAPB | RPS13 | C13ORF23 | RPL19 | P4HB | DNAJC5 |
| RPL15 | ZDHHC19 | WDR37 | DACH1 | WWP1 | RPL15 | GOLGA1 |
| RPS13 | EXT1 | ZNF17 | AMD1 | ARG1 | ZNF17 | CD59 |
| WDR37 | ZNF608 | ANKS1A | SLC26A8 | CKAP4 | EIF3D | RPS15 |
| ANKS1A | TBC1D8 | CD59 | WDR37 | EXOC7 | MMP9 | ARG1 |
| KIF1B | RRBP1 | CKAP4 | KIF1B | PGD | SLC36A1 | EMILIN2 |
| MMP9 | ATP8B4 | PFKFB2 | WWP1 | HK3 | NAPB | HIBADH |
| EXOC7 | RPS3A | RPL22 | RPS25 | RRBP1 | ARID5B | MUC1 |
| CMTM4 | RPL27A | ZC3H3 | RPL24 | RPL26 | HK3 | ZC3H3 |
| RPL24 | PHTF1 | ZDHHC19 | ZNF608 | FAM160A2 | CSGALNACT2 | ZDHHC19 |
| CSGALNACT2 | FBXO34 | NLRC4 | RRBP1 | CTDP1 | FAM160A2 | HK3 |
| ATP2A2 | CYP1B1 | RRBP1 | NSUN7 | RPL27A | RPS3A | PHCA |
| FAM160A2 | RPL4 | RPL26 | TDRD9 | NT5DC2 | RPL27A | NSUN7 |

Figure 4:
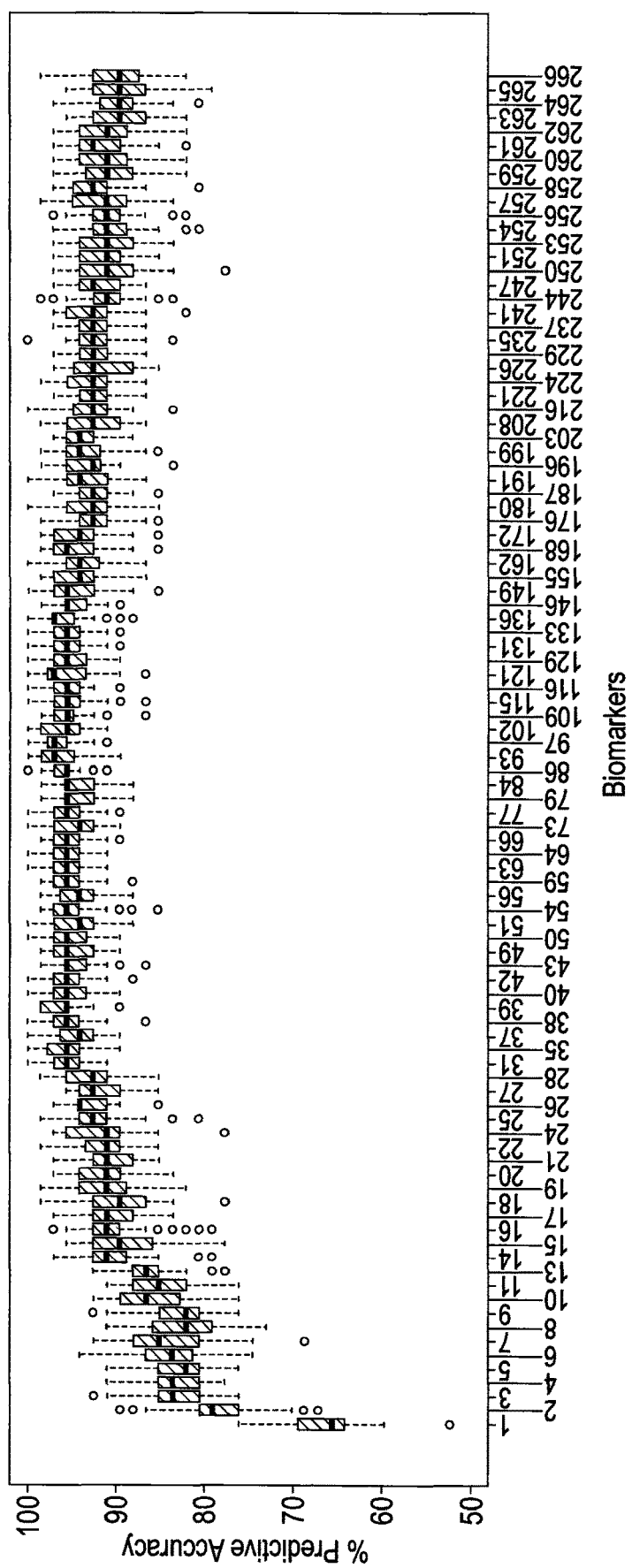
FIG. 4 is a graph and table indicating the predictive accuracies for different subsets of biomarkers selected from the 266 biomarkers in Table 1.

Having regard to FIG. 4, 98 subsets of different numbers of biomarkers were formed from the entire panel of 266 genes, wherein each subset was characterised by only including genes of a particular level of abundance in the top 1000 subsets selected from the 44,014. The subsets range from a single gene (LDLR, which was by far the most abundant) to the whole panel of 266 biomarkers. Where multiple genes have the same abundance they are all included in a single subset associated with that threshold, which is why there are less subsets than there are total genes. The trend, derived from a more basic ANN than that detailed in Table 2, shows an increase in predictive accuracy with increasing subset size, which begins to plateau at a subset size of 97 genes. Here a maximum predictive accuracy is reached at 97.0%. When the subset size exceeds 149 genes the predictive accuracy begins to drop off, falling to 89.6%. This trend does not match that obtained using a random forest, although here we examine single defined subsets rather than many random ones. Of the three subsets reaching the maximum predictive accuracy, the smallest one (subset 50) contains genes that appeared 165 times or more in the top 1000 subsets of the test.

Through use of systems-scale profiling technology, this study identified biomarker signatures predictive of the development of post-operative sepsis with high accuracy in a sizable blinded validation set. The key to analysing complicated data sets is the method of analysis. Our approach was predicated on the conclusion that no one biomarker is likely to be a predictive for sepsis in humans. Previous studies of pre-symptomatic biomarker expression have shown that conventional linear analyses of biomarker expression may fail to reveal differences between the two patient groups i.e. sepsis and non-sepsis patients. A variety of Non-linear techniques were used with varying degrees of success to differentiate between the transcriptomes of patients who go on to develop sepsis and their comparators. Random Forests and SVM demonstrated some use for the differentiation of transcriptomes from different patient groups. However, ANN analysis, using 25 and 44 gene biomarker signatures performed excellently. These gave high predictive accuracies as well as high sensitivities and specificities when differentiating between patients who went on to develop sepsis and their comparators. Furthermore, the biomarker signatures derived were very robust when tested against potentially confounding transcriptomes from patients who had SIRS but who did not go on to develop sepsis.

The strong performance of non-linear techniques is perhaps not unexpected, since immune markers fluctuate greatly over the entire course of sepsis. It is unlikely that analysis using simple linear techniques could be used as easily to pick out key biomarker signatures.

It is also worth noting that the successful testing of patient transcriptomes through use of a multiplexed q RT-PCR indicates the suitability of this technology for further development as a diagnostic assay.

The functional relevance of a subset of transcripts constituting this signature, which is broadly associated with coordinated molecular and cellular chain of events involved during inflammation and sepsis, instills confidence in our results. Indeed activation of the complement pathway has been shown to play an important role in sepsis and inflammation. Conversely, dendritic cells and other antigen presenting cells have been shown to disappear from the circulation during septic episodes, which may account for the observed decrease in abundance of transcripts associated with MHC gene expression. It should be noted that the majority of the candidate markers identified through this unbiased global profiling approach have not been as well characterized as these few functionally enriched "landmark" transcripts.

The invention claimed is:

1. A diagnostic kit for predicting development of sepsis prior to onset of symptoms, comprising reagents for detecting nucleic acid gene products or expression levels of members of a biomarker signature consisting of 266 genes of Table 1 in a sample obtained from a patient at a risk of sepsis,
   wherein the reagents comprise one or more of fluorescently labelled oligonucleotide probes or fluorescently labeled primers,
   wherein the fluorescently labelled oligonucleotide probes or fluorescently labeled primers consist of probes and primers each capable of specific binding and detection of gene products of at least 25 of the members of the biomarker signature,
   and wherein the at least 25 of the members of the biomarker signature comprise ACTR6, BIN1, C16ORF7, CD247, CLNS1A, CYB561, FCER1A, GRB10, HS.445036, LARP5, LOC646766, MRPL50, ADRB2, BOAT, C21ORF7, CD3D, CPA3, DHRS3, FLT3LG, GTPBP8, ICAM2, LDHA, LOC652071, MRPS27 and AKR1B1.

2. A system for analysis of a biological sample obtained from a patient at risk of sepsis to predict or monitor development of sepsis in the patient, the system comprising:
   a detector for monitoring, measuring or detecting the nucleic acid gene products or the expression levels of the members of a biomarker signature;
   the kit of claim 1;
   and a computer processor configured to analyze data produced by the detector, and to provide an output.

3. The kit of claim 1, wherein the patient is a post-surgical patient, an immunocompromised individual, an intensive-care patient or a burn patient.

4. The kit of claim 1, wherein the at least 25 of the members of the biomarker signature further comprise BTBD11, C5ORF39, CD3E, CR1, DIP2A, GALM, HDC, ICOS, LDOC1, LSG1, AMPH, C11ORF1, C9ORF103, CD6, CRIP2, EBI2, GAS7, HIST2H4B and IL1R1.

5. The kit of claim 1, wherein the reagents comprise the fluorescently labelled oligonucleotide probes.

6. The kit of claim 1, wherein the reagents comprise the fluorescently labelled primers.

7. A diagnostic kit for predicting development of sepsis prior to onset of symptoms, comprising reagents for detecting gene products or expression levels of members of a biomarker signature in a sample obtained from a patient at a risk of sepsis,
   wherein the biomarker signature consists of 266 genes of Table 1,
   wherein the reagents comprise a microarray with immobilized probes, the probes consisting of probes each suitable for specific binding to and detection of gene products of at least 25 of the members of the biomarker signature,
   and wherein the at least 25 of the members of the biomarker signature comprise ACTR6, BIN1, C16ORF7, CD247, CLNS1A, CYB561, FCER1A, GRB10, HS.445036, LARP5, LOC646766, MRPL50, ADRB2, BOAT, C21ORF7, CD3D, CPA3, DHRS3, FLT3LG, GTPBP8, ICAM2, LDHA, LOC652071, MRPS27 and AKR1B1.

8. The kit of claim 7, wherein the gene products are nucleic acids.

9. The kit of claim 7, wherein the gene products are proteins.

10. A system for analysis of a biological sample obtained from a patient at risk of developing sepsis to predict or monitor development of sepsis in the patient, the system comprising:
    a detector for monitoring, measuring or detecting the gene products or the expression levels of the member of a biomarker signature;
    the kit of claim 7;
    and a computer processor configured to analyze data produced by the detector, and to provide an output.

11. The kit of claim 1, wherein the nucleic acid gene products are transcribed ribonucleic acids or cDNA.

12. The kit of claim 8, wherein the nucleic acids are transcribed ribonucleic acids or cDNA.

13. The kit of claim 7, wherein the at least 25 of the members of the biomarker signature consist of all 266 genes of Table 1.

14. The kit of claim 7, wherein the at least 25 of the members of the biomarker signature further comprise BTBD11, C5ORF39, CD3E, CR1, DIP2A, GALM, HDC, ICOS, LDOC1, LSG1, AMPH, C11ORF1, C9ORF103, CD6, CRIP2, EBI2, GAS7, HIST2H4B and IL1R1.

15. The kit of claim 1, wherein the at least 25 of the members of the biomarker signature consist of all 266 genes of Table 1.

* * * * *